(12) United States Patent
Luo

(10) Patent No.: US 12,239,790 B1
(45) Date of Patent: Mar. 4, 2025

(54) MODULAR ELBOW FRAME ASSEMBLY FOR A VENTILATOR

(71) Applicant: DCSTAR INC., New York, NY (US)

(72) Inventor: David Luo, New York, NY (US)

(73) Assignee: DCSTAR INC., New York, NY (US)

( * ) Notice: Subject to any disclaimer, the term of this patent is extended or adjusted under 35 U.S.C. 154(b) by 0 days.

(21) Appl. No.: 18/515,604

(22) Filed: Nov. 21, 2023

(51) Int. Cl.
*A61M 16/08* (2006.01)
(52) U.S. Cl.
CPC . *A61M 16/0816* (2013.01); *A61M 2210/0606* (2013.01)
(58) Field of Classification Search
CPC ........ A61M 16/0816–0833; A61M 2210/0606
See application file for complete search history.

(56) References Cited

U.S. PATENT DOCUMENTS

| 2015/0217074 A1* | 8/2015 | Wells | D04B 21/18 128/207.18 |
| 2018/0236200 A1* | 8/2018 | Goldspink | A61M 16/0057 |
| 2018/0289910 A1* | 10/2018 | Flower | A61M 16/021 |
| 2019/0290878 A1* | 9/2019 | Romagnoli | A61M 16/1045 |
| 2020/0345963 A1* | 11/2020 | Barlow | A61M 16/0816 |
| 2021/0353890 A1* | 11/2021 | Tiwari | A61M 16/0622 |
| 2023/0181856 A1* | 6/2023 | Lee | A61M 16/0683 128/206.24 |

FOREIGN PATENT DOCUMENTS

WO  WO-2023015340 A1 * 2/2023 ........ A61M 16/0688

* cited by examiner

*Primary Examiner* — Elliot S Ruddie
(74) *Attorney, Agent, or Firm* — HSML P.C.

(57) ABSTRACT

A modular elbow frame assembly for a ventilator, which includes an elbow, a hose, a tubular connector, an external connecting component, a frame, a noise reduction element, a quick-release device. The modular elbow frame assembly for a ventilator can be used in conjunction with a patient interface cushion and a ventilator tube. In this system, the quick-release device is integrally formed with the elbow. The assembly involves a modular design that makes the elbow detachable, allowing the replacement of the elbow with exhaust holes of different numbers or diameters for patients to adjust airflow pressure into the airway. The quick-release device enables the rapid detachment between the elbow and the frame or patient interface cushions. Patients can choose whether to include the noise reduction element and whether to connect the ventilator tube via a hose or directly through a tubular connector.

19 Claims, 26 Drawing Sheets

MODULAR ELBOW FRAME ASSEMBLY FOR A VENTILATOR

TECHNICAL FIELD

This disclosure pertains to the field of medical devices technology, particularly relating to a modular elbow frame assembly for a ventilator, configured to be used along with patient interface cushions such as a face mask or a nasal mask. It works in coordination to deliver pressurized gas from the ventilator into the patient's airway for therapeutic purposes.

BACKGROUND

Obstructive Sleep Apnea (OSA) is a common sleep-related breathing disorder that can affect anyone. An apneic event is defined as a cessation of airflow through the mouth and nose lasting more than 10 seconds. If there are more than 30 such episodes in seven hours of sleep or if the Apnea-Hyponea Index (AHI) exceeds five times, accompanied by daytime symptoms such as fatigue and excessive sleepiness, it can be diagnosed as Obstructive Sleep Apnea Syndrome. Sleep apnea causes sufferers to experience long-term deprivation of fresh air, leading to reduced blood oxygen levels and increased blood viscosity. This situation can damage the lungs, heart, and other organs, potentially resulting in hypertension, coronary heart disease, cerebrovascular disease, emotional disorders, dry mouth, pharyngitis, and other health issues.

Continuous Positive Airway Pressure (CPAP) therapy is a common and effective treatment method for patients with OSA. This treatment involves using a CPAP machine to deliver steady positive pressure. The machine uses a mechanical pump to compress gas at a single pressure level, which is then delivered through an airflow conduit and an elbow to act on the pharynx. This increases the positive pressure in the patient's throat, thereby countering the negative pressure of inhalation. To reduce the resistance to inhalation, the airflow entering the patient's pharynx stimulates the upper airway pressure and the body's mechanoreceptor. This increases the tension in the patient's upper airway dilator muscles, preventing the collapse of the upper airway, maintaining its openness, and eliminating local tissue edema.

The exhaust holes for expelling the patient's exhaled gas are typically set on the elbow that connects the ventilator tube and the frame or patient interface cushion. It aims to prevent the re-accumulation of exhaled carbon dioxide, providing air circulation for the patient's exhaled gas. When the airflow is expelled into the external environment through exhaust holes in the elbow, some noise is generated. The noise not only affects the patient's user experience but also the sleep quality of his/her companion. Airflow noise are entirely different from and sound in statistical and spectral features. One source of the noise is the collision between the airflow exiting the vent and the external air currents, creating disturbances in the flow of air, or resulting from the friction between the outgoing airflow and surrounding objects. The exhaust holes of the elbow contribute to the partitioning of the airflow. With higher airspeed, turbulence intensifies, often manifesting as increased wind noise. Furthermore, the wind noise increases as airspeed grows. Common elbow designs can provoke a backlash of airflow at the outlet gaps, producing substantial wind noise. This phenomenon doesn't merely affect patients emotionally and mentally but also poses a genuine threat to their well-being.

Moreover, the formation of noise in the elbow is also related to the total diameter of the outlet holes. The elbows currently available on the market come with a predetermined number and diameter of exhaust holes, offering no room for customization based on patient preferences. Those standard elbows constrain patients to adapt to virtually identical breathing pressures, regardless of the CPAP settings, thereby impeding their ability to opt for a personalized treatment approach that aligns with their specific needs.

During the flow of gas, maintaining the integrity of sealed interface connections poses a significant challenge. The sealing structure of patient interface cushions, including face masks or nasal masks used in positive pressure therapy, are susceptible to be affected by the air pressure, which can result in compromised sealing. To fortify these seals, connections between tubes and masks are typically constructed as a single, unified entity. Yet, this design introduces complications due to the considerable distance between the CPAP therapy device and the patient's airway, often resulting in tangled tubing and separation difficulties. For comfort and ease of use, manufacturers have developed detachable elbows that separate from masks, enhancing patients' nocturnal mobility. However, these current elbows continue to face hurdles during disconnection and reattachment, with seal integrity between the elbow, patient interface, and tubing interface often falling short of reliability.

There is a notable gap in the market for modular elbow frame assemblies that facilitate quick disassembly. The disclosure, as discussed herein, provides an innovative, quickly detachable modular elbow frame assembly, capable of adapting to diverse airflow pressures. This new option furnishes patients with a much-needed alternative, elevating the convenience and accessibility of CPAP therapy.

SUMMARY

This disclosure aims to address the existing deficiencies of the current designs and to provide a modular elbow frame assembly for a ventilator.

In an embodiment, a modular elbow frame assembly for a ventilator is provided for delivering positive pressure breathing gas to a patient's airway. A modular elbow frame assembly for a ventilator has the following features:

A modular elbow frame assembly for a ventilator includes a hose for connection to a ventilator tube, an elbow that connects the hose and a patient interface cushion for a delivery of pressurized gas to the patient's airway, and a quick-release device for detachably connecting the elbow and the patient interface cushion.

The elbow has a first connector and a second connector, with a junction between the first connector and the second connector being curved.

The quick-release device is situated on the first connector of the elbow and integrally formed with the elbow, enabling the first connector to be detachably connected with the patient interface cushion via the quick-release device.

One end of the hose is detachably connectable to the second connector of the elbow, while the other end is connected to the ventilator tube, configured to channel pressurized gas through the elbow into the patient's airway for respiration.

There is at least one vent present on the elbow, which is configured to release a continuous flow of exhaled gas from the patient to the external environment. The vent on the elbow includes several exhaust holes, facilitating communication between the elbow and the external environment, allowing for the exhaled gas from the patient to be emitted outside the elbow, e.g. to the external environment, with a maximum total surface area of the exhaust holes not exceeding 5 cm$^2$.

The elbow weighs no more than 20 g.

A portion of the outer wall of the second connector fits against an inner wall of the hose upon a connection of the elbow with the hose.

In one embodiment, the quick-release device has a pair of protruding pieces, each respectively positioned on two sides of the first connector and extending outward, with two front ends forming hook sections. And the patient interface cushion includes a fixed part for attachment and coverage by the hook sections, with an annular positioning arm on the outer edge surface of the first connector. The fixed part of the patient interface cushion embeds into the annular positioning arm and the hook sections, facilitating the rotational connection between the patient interface cushion and the first connector.

In one embodiment, the hose has a first end nearer the elbow, a second end away from the elbow, and a spiral tube provided between the first end and the second end, consisting of several adjacent coils. The hose is detachably connectable to the elbow via the first end, thereby channeling gas pressurized by the ventilator into the patient's airway.

In one embodiment, the elbow and the first end of the hose are detachably connectable through a snap-fit.

In one embodiment, the elbow and the first end of the hose are detachably connected through magnetic attraction.

In one embodiment, the second end of the hose connects to the ventilator tube, and a rotating component is configured on the second end of the hose, providing a rotational connection between the hose and the ventilator tube.

In one embodiment, an axis of the exhaust holes forms an angle α of at or between 0 to 45° with the symmetrical axis of the first connector of the elbow, guiding the exhaled gas from the patient outward.

In another embodiment, a modular elbow frame assembly for a ventilator is provided for delivering positive pressure breathing gas to a patient's airway. A modular elbow frame assembly for a ventilator has the following features:

A modular elbow frame assembly for a ventilator includes a hose for connection to a ventilator tube, a frame for connection to a patient interface cushion, an elbow that connects the hose and the frame for a delivery of pressurized gas to the patient's airway, and a quick-release device for detachably connecting the frame and the elbow.

The elbow has a first connector and a second connector, with a junction between the first connector and the second connector being curved, and the first connector configured to detachably connect to the frame.

The quick-release device is situated on the first connector of the elbow and integrally formed with the elbow, enabling the elbow to be detachably connectable to the frame through the quick-release device.

One end of the hose is detachably connectable to the second connector of the elbow, while the other end is connected to the ventilator, configured to channel pressurized gas through the elbow into the patient's airway for respiration.

The frame includes a fixed opening for connection with the elbow, incorporating a receiving structure configured to receive the quick-release device on the elbow.

There is at least one vent present on the elbow, which is configured to release a continuous flow of exhaled gas from the patient to an external environment. The vent on the elbow includes several exhaust holes, facilitating communication between the elbow and the external environment, allowing for the exhaled gas from the patient to be emitted outside the elbow, e.g., to the external environment. The total surface area of exhaust holes accounts for at or between 3% to 50% of a surface area of the elbow.

In one embodiment, the fixed opening has at least one of the following features: a perimeter of the fixed opening at or between 10 to 120 mm; an area of the fixed opening at or between 5% to 50% of the external surface area of the frame not facing the patient's face; a diameter of the fixed opening at or between 3 to 40 mm; a wall thickness of the fixed opening at or between 0.3 to 5 mm.

In another embodiment, a modular elbow frame assembly for a ventilator is provided for delivering positive pressure breathing gas to a patient's airway. A modular elbow frame assembly for a ventilator has the following features:

A modular elbow frame assembly for a ventilator includes a tubular connector for connection to a ventilator tube, an elbow that connects tubular connector and a patient interface cushion for a delivery of pressurized gas to the patient's airway, and a quick-release device for detachably connecting the elbow and the patient interface cushion.

The elbow has a first connector and a second connector, with a junction between the first connector and the second connector being curved.

The tubular connector is detachably connectable to the second connector of the elbow. And the second connector and the tubular connector is joined to create an airflow passage for receiving and transporting positive pressure airflow from the ventilator tube to the patient through the patient interface cushion.

There is at least one vent present on the elbow, which is configured to release a continuous flow of exhaled gas from the patient to an external environment. The vent on the elbow includes several exhaust holes, facilitating communication between the elbow and the external environment, allowing for the exhaled gas from the patient to be emitted outside the elbow, e.g., to the external environment. And the ratio, whether calculated as the diameter of the outer interface that contacts external air divided by the diameter of the inner interface devoid of such contact, or vice versa, is less than 2.45 for at least part of the exhaust holes.

In an embodiment, the tubular connector includes a first port connected to the ventilator tube and a second port connected to the elbow. The tubular connector is detachably connected to the ventilator tube and the elbow through the first port and the second port.

In an embodiment, an inner diameter or an outer diameter of the first port of the tubular connector corresponds to an outer diameter or an inner diameter of the second connector for connecting the same, ensuring the sealed passage of the positive pressure gas through the tubular connector.

In an embodiment, the first port connected to the ventilator tube is configured as a 22 mm or 15 mm diameter port, compatible with the ventilator tube.

In another embodiment, a modular elbow frame assembly for a ventilator is provided for delivering positive pressure breathing gas to a patient's airway. A modular elbow frame assembly for a ventilator has the following features:

A modular elbow frame assembly for a ventilator includes a hose for connection to the ventilator tube, an elbow that connects the hose and a patient interface cushion or a frame for a delivery of pressurized gas to the patient's airway, a quick-release device for detachably connecting the elbow with the patient interface cushion or the frame, and an external connecting component for noise reduction.

The elbow has a first connector and a second connector, with a junction between the first connector and the second connector being curved. The first connector is configured to be detachably connectable to the patient interface cushion or the frame.

The hose is detachably connectable to the second connector of the elbow. And the second connector and the hose is joined to create an airflow passage for receiving and transporting positive pressure airflow from the ventilator tube to the patient through the patient interface cushion.

The external connecting component includes an internal noise reduction element, including a main body detachably connectable to the elbow, and an opening set at the center of the main body to accommodate the noise reduction element, with the main body having snap buckles on both sides which are snap-fittable onto the elbow.

There is at least one vent present on the elbow, which is configured to release a continuous flow of exhaled gas from the patient to an external environment. The vent on the elbow includes several exhaust holes, facilitating communication between the elbow and the external environment, allowing for the exhaled gas from the patient to be emitted outside the elbow, e.g., to the external environment. The noise reduction element is positioned between the vent of the elbow and the main body of the external connecting component, secured behind the opening of the main body.

In an embodiment, the noise reduction element can include a noise reduction cotton or a noise reduction mesh, with the noise reduction cotton being made of one type of fibrous sound-absorbing material or foam sound-absorbing material, and the noise reduction mesh being made of fabric or nylon.

In an embodiment, the noise reduction component has at least one of the following features: a thickness of no more than 9 mm, a weight of no more than 7 g.

In an embodiment, a noise reduction cotton is additionally provided between the vent of the elbow and the external connecting component.

In an embodiment, the noise reduction element is detachably connectable within the opening of the main body by one of the following methods: a snap-fit connection, a knob, or a clip.

In an embodiment, the noise reduction element is permanently affixed within the opening of the main body by one of the following methods: injection molding, ultrasonic welding, heat pressing, or adhesive bonding.

In another embodiment, a modular elbow frame assembly for a ventilator is provided for delivering positive pressure breathing gas to a patient's airway. A modular elbow frame assembly for a ventilator has the following features:

A modular elbow frame assembly for a ventilator includes a hose for connection to a ventilator tube, a frame for connection to a patient interface cushion, an elbow that connects the hose and the frame for a delivery of pressurized gas to the patient's airway, and a quick-release device for detachably connecting the frame and the elbow.

The elbow has a first connector and a second connector, with a junction between the first connector and the second connector being curved, and the first connector configured to detachably connect to the frame. The first connector and the second connector of the elbow are joined to create an airflow passage, allowing the positive pressure airflow to pass through an inlet end and an outlet end of the elbow while maintaining a seal, providing ventilatory support.

The quick-release device is set on the first connector of the elbow and integrally formed with the elbow, and the elbow is detachably connectable to the frame through the quick-release device.

The frame has a vent for the continuous flow of exhaled gas from the patient to the external environment, with several exhaust holes positioned at the vent of the frame, the frame communicating with the external environment through the exhaust holes, thereby discharging exhaled gas from the patient outside the frame, e.g., the external environment.

In one embodiment, a receiving structure of the frame and the first connector of the elbow includes magnets for mutual attraction, and the frame and the elbow are connectable by magnetic force.

The benefits of the modular elbow frame assembly for a ventilator provided by this disclosure can include:

1) By employing a detachable, modular design for the elbow, the assembly accommodates the diverse requirements and preferences of patients with OSA concerning air pressure. This design elevates the comfort of treatment, enabling patients to choose between elbows of varying diameters or numbers of exhaust holes to adjust airflow pressure, particularly when the ventilator fails to deliver the ideal pressure conditions. Given that patients have distinct airflow pressure requirements, this disclosure allows patients to select an elbow that aligns with their needs, making Continuous Positive Airway Pressure (CPAP) therapy more comfortable. Furthermore, this disclosure provides specialized options for patients experiencing respiratory insufficiency or failure, offering the choice to opt for a hole-free elbow to better accommodate their unique circumstances.

2) The quick-release feature of this design improves the flexibility and convenience for patients undergoing therapy, facilitating the swift detachment of the elbow from the frame or patient interface cushions, including a nasal mask, a face mask, a nasal pillow, or a nasal cradle mask. By adding releasable functions among the therapeutic components, the design simplifies the routine of donning and doffing, particularly beneficial for patients who need to rise at night or momentarily step away from their resting area. And it eliminates the need for cumbersome steps such as unfastening head straps or extracting the patient interface cushion, thereby streamlining laborious adjustment procedures. Moreover, the design ensures a releasable yet stable connection between the elbow and the frame or patient interface cushions, supplemented by the capability for mutual rotation. The second connector of the elbow is configured to rotate in relation to the hose or the tubular connector, thereby improving patient maneuverability. Such features accommodate diverse wearing preferences, prevent the inconvenience of hose tangling, and overall, heighten the user experience by providing increased comfort and ease of use for patients.

3) The modular design of an external connecting component that allows for the detachable connection with the elbow empowers patients with the flexibility to incorporate or forgo the noise reduction element, catering to individual preferences. For those disinclined towards noise reduction materials, the structure allows for straightforward disassembly. If the external connecting component or noise reduction materials incur damage, they can be replaced separately without the need to substitute the entire elbow unit. This not only enhances the durability of the elbow but also simplifies its maintenance. Furthermore, patients can select from an assortment of noise reduction materials, such as noise reduction cotton or noise reduction mesh, allowing them to opt for different noise reduction effects and usage experiences. The user-friendly, detachable design also addresses common hygiene concerns, eliminating hard-to-clean recesses and ensuring that all components are replaceable, promoting a cleaner, more sanitary usage environment.

4) The modular elbow design provides patients with different connection alternatives, featuring a detachable connection between the second connector of the elbow and the hose. This allows patients to choose between attaching the hose to the elbow prior to connecting the hose to the ventilator tube, or using a tubular connector appropriate for the specific diameter of the ventilator tube port to establish a direct link between the elbow and the ventilator tube. Factors like the hose length and tube size can influence patients' comfort during the use of therapeutic components. Some might appreciate an extended hose for greater mobility, while others might prefer the enhanced airflow from the ventilator tube. The use of a tubular connector grants patients greater autonomy to select the configuration that enhances their comfort during therapy, offering different options for patients with various preferences, enhancing user-friendliness and providing more choices for the patients. Furthermore, this design reduces the need for complete component replacements, decreasing carbon dioxide emissions. Additionally, the modular detachable design is space-efficient during logistics and transportation by allowing uniform stacking and it also aligns with sustainable and eco-friendly design principles.

LABELING IS AS FOLLOWS

1—Modular elbow frame assembly for a ventilator; 2—Elbow; 21—External connecting component; 22—Quick-release device; 221—Hook sections; 23—First connector; 24—Second connector; 25—Annular positioning arm; 3—Hose; 31—First end; 32—Tubular connector; 321—First port; 322—Second port; 33—Second end; 4—Vent; 41—Noise reduction element; 412—Thickness of noise reduction material; 5—Head strap; 6—Opening for external connecting component; 61—Snap buckle; 7—Patient interface cushion; 8—Frame; 81—Fixed opening; 82—Receiving structure.

DETAILED DESCRIPTION

To facilitate an understanding of this disclosure, a more comprehensive description will be provided below with reference to the relevant drawings. The drawings present typical embodiments of this disclosure. However, it should be understood that the disclosure can be implemented in many different forms and is not limited to the embodiments described herein. Rather, these embodiments are provided to make the disclosure more thorough and comprehensive.

As shown in FIG. 1 to FIG. 26, this disclosure provides a modular elbow frame assembly 1 for a ventilator, which is configured to deliver positive pressure breathing gas to a patient's airway.

Figure 4:
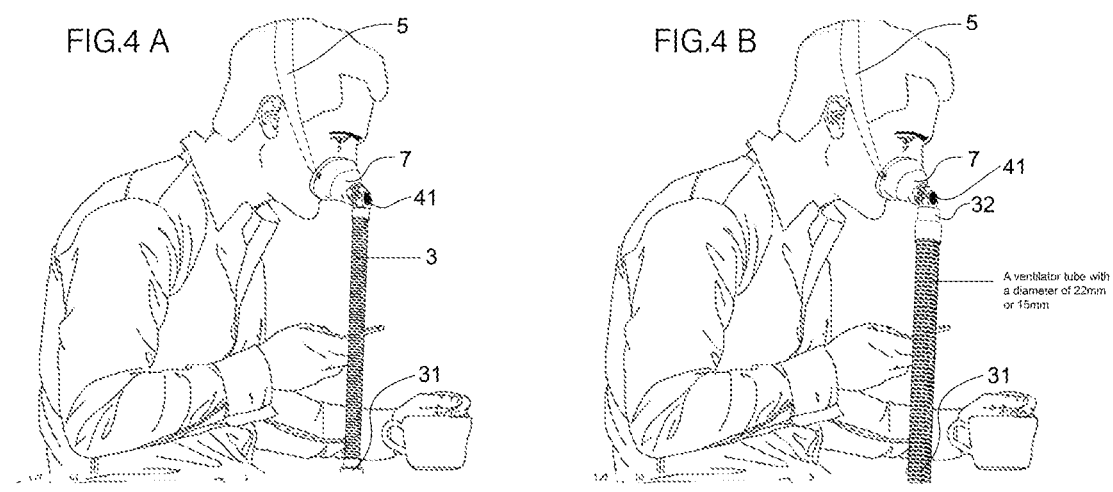
FIG. 4A and FIG. 4B are schematic diagrams displaying usage scenario of the modular elbow frame assembly for a ventilator in accordance with an example embodiment.
Figure 26:
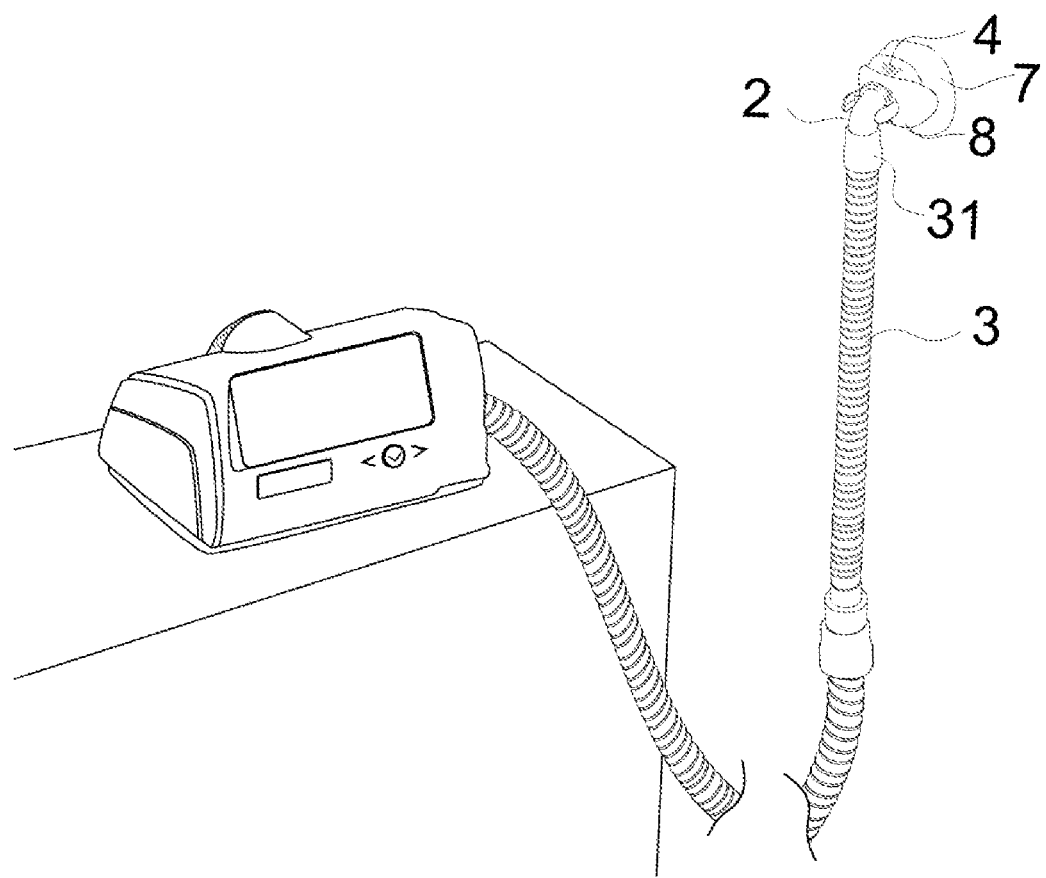
FIG. 26 is a schematic diagram showing the use of a modular elbow frame assembly for a ventilator in accordance with an example embodiment.

In the following embodiments of the modular elbow frame assembly 1 for a ventilator, during use, the patient interface cushion 7 is first fitted against the patient's face, creating an airflow passage between the patient interface cushion 7 and the patient's airway, thereby sealingly delivering positive pressure gas into the patient's airway. Subsequently, patients can choose to secure the frame 8 to the surface of the patient interface cushion 7, then secure the head strap 5 to the frame 8 and wear the head strap 5 on the head to ensure that the patient interface cushion 7 remains in place on the patient's face without falling off or shifting. Alternatively, patients can also choose not to use the frame 8 and directly secure the patient interface cushion 7 to the face using the head strap 5. Then, with a quick-release device 22 on the elbow 2, the elbow 2 can be connected to the frame 8 attached to the patient interface cushion 7 such as a face mask or nasal mask (if the frame 8 is not used, the elbow 2 is directly connected to the patient interface cushion 7). Finalizing the assembly involves connecting the hose 3. As illustrated in FIG. 26, in this way, the ventilator's pressurized air is channeled through the hose 3, passing through the elbow 2, then reaches the face mask or nasal mask on the patient interface cushion 7. This setup guarantees an uninterrupted, smooth transit of positive pressure gas from the ventilator tube into the patient's airway. If necessary, patients can opt for incorporating a tubular connector 32, detachably connectable to the elbow 2 at the second connector 24. The connection between the second connector 24 and the tubular connector 31 establishes an airflow passage to deliver the positive pressure gas from the ventilator tube, coursing through the elbow 2, to the patient interface cushion 7 for respiration. Moreover, patients can opt to install an external connecting component 21. This component features a main body detachably connectable to the elbow 2 and has an opening located centrally on the main body to accommodate the noise reduction element 41. The main body has snap buckles 61 on both sides which are snap-fittable onto the elbow 2. In this assembly, the noise reduction element 41 is positioned between the vent 4 of the elbow 2 and the main body of the external connecting component 21 (as illustrated in FIG. 4), secured behind the opening of the main body. Such design increases the patient's freedom of choice, thereby addressing varied preferences and promoting an optimized user experience.

Figure 7:
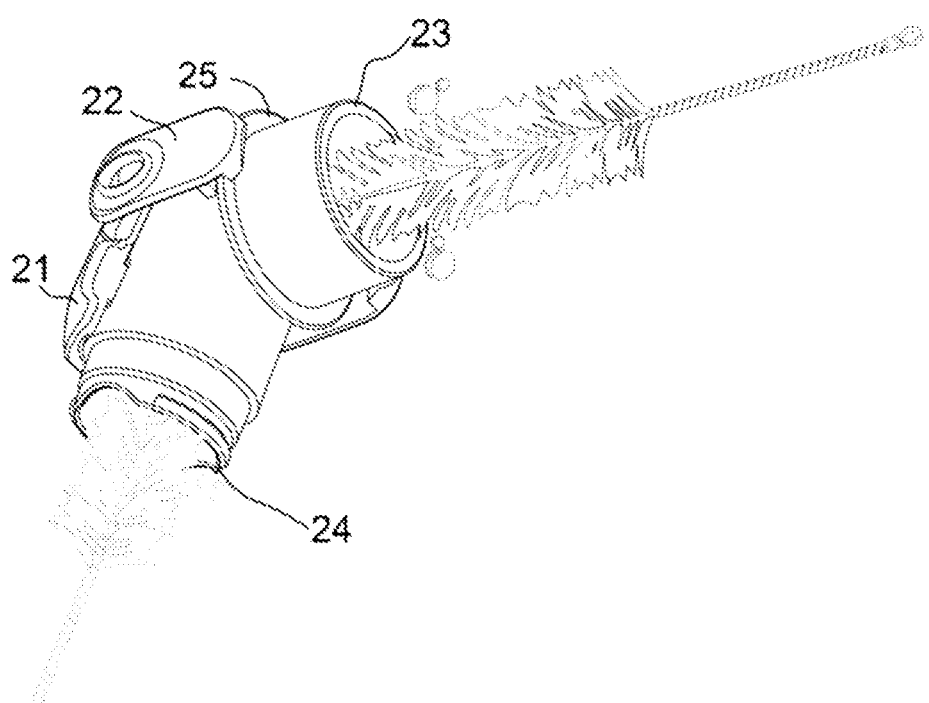
FIG. 7 is a schematic diagram depicting the cleaning of the elbow component within the modular elbow frame assembly for a ventilator in accordance with an example embodiment.
Figure 8:
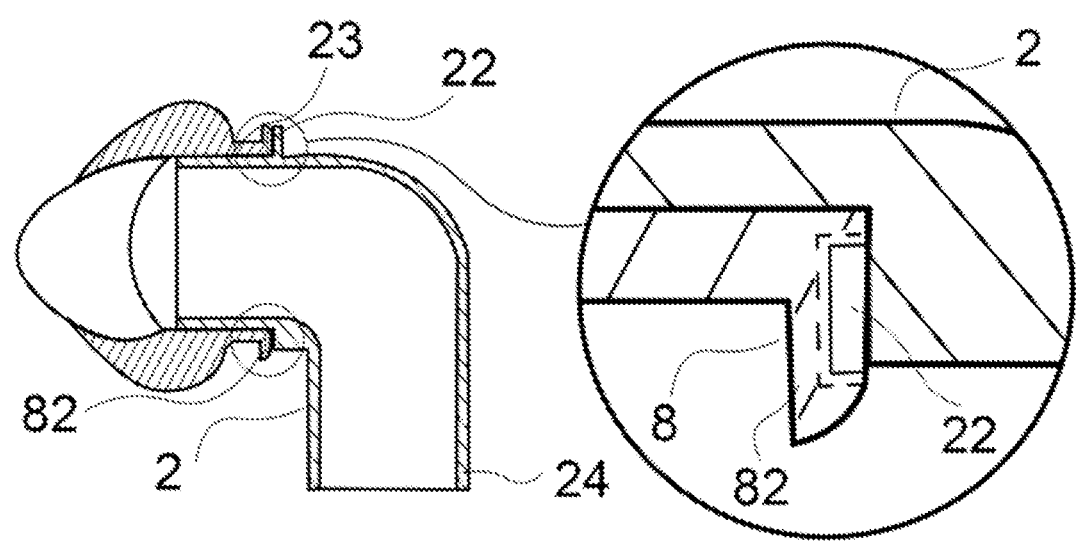
FIG. 8 is a schematic diagram showing the adsorptive connection between the frame and the elbow in the modular elbow frame assembly for a ventilator in accordance with an example embodiment.
Figure 9:
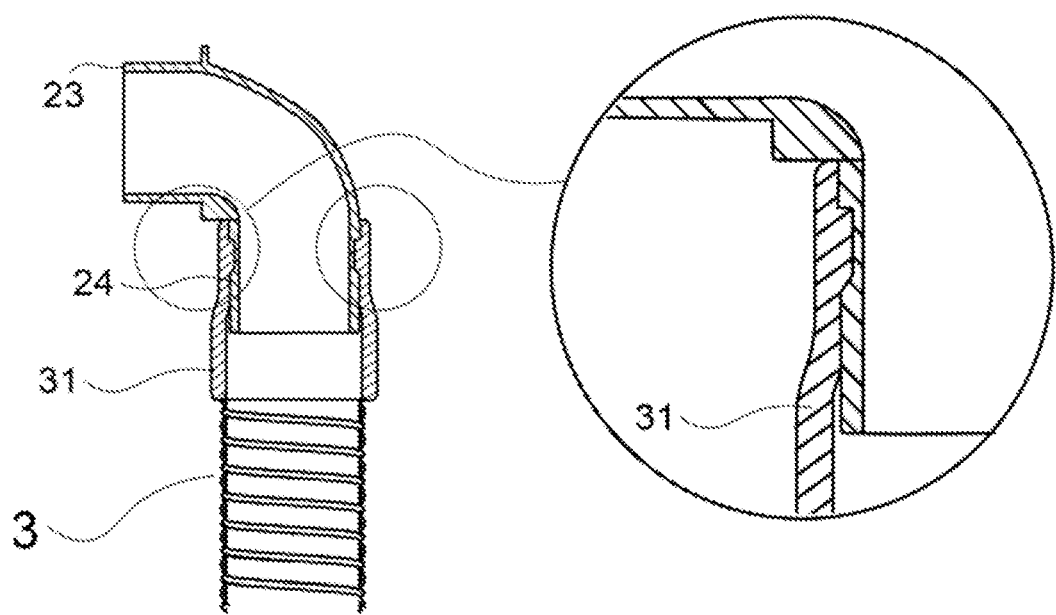
FIG. 9 is a schematic diagram illustrating the snap-fit connection between the hose and the elbow of the modular elbow frame assembly for a ventilator in accordance with an example embodiment.

The modular elbow frame assembly 1 for a ventilator has several positions for detachable connection, ensuring the elbow 2 and the patient interface cushion 7 maintain hygiene. Patients can easily disassemble and clean the elbow 2, specifically at the first connector 23 and the second connector 24. Existing models, whether they feature detachable or fixed elbows, tend to have complex structures that pose challenges in thorough cleaning, thereby compromising hygiene assurance. In contrast, the elbow 2 of this disclosure has a simple structure. Beyond ease of use, this disclosure offers patients the added advantage of completely disassembling the elbow 2 for comprehensive cleaning and sterilization. This design prevents dirt and bacterial buildup at the junction, ensuring the product's hygiene. By mitigating the harboring of contaminants, the assembly reduces the risk of infections in patients (as depicted in FIG. 7).

Embodiment 1

As illustrated in FIG. 1 to FIG. 3, FIG. 5 to FIG. 6, FIG. 8 to FIG. 10, and FIG. 24, in this embodiment, the modular elbow frame assembly 1 for a ventilator includes: a hose 3 for connection to a ventilator tube, a frame 8, an elbow 2 set between the hose 3 and the frame 8 for delivering pressurized gas to the patient's airway, and a quick-release device 22 for detachably connecting the elbow 2 to the patient interface cushion 7. The elbow 2 has a first connector 23 and a second connector 24, wherein the junction between the first connector 23 and the second connector 24 is curved. The first connector 23 is detachably connectable to the frame 8.

In this embodiment, the overall design of the elbow 2 is compact and lightweight, with any given cross-sectional diameter of at or between 10 to 50 mm, and an overall height of at or between 15 to 60 mm. Due to the uniformity of the wall thickness and the height restriction of the elbow 2 in the overall design, excessive weight of the component is effectively avoided. Specifically, the central axis of the first connector 23 and that of the second connector 24 form an angle of at or between 10° and 170°. This design facilitates a smoother connection between the patient interface cushion 7 and the hose 3, avoiding the airflow obstruction due to improper angling of the elbow 2 or the hose 3 being made from overly soft material, also preventing noise due to turbulent airflow within the tube through correctly guiding the direction of the airflow. Part of the elbow 2 is at least rigid to some extent, while the remaining parts can deform to achieve a snap-fit. The elbow 2 can be made from one or a combination of medical materials such as polycarbonate, polyethylene, polypropylene, acrylonitrile butadiene styrene or silicone.

The elbow 2 has at least one vent 4, positioned at the second connector 24 of the elbow. The vent 4 is to facilitate the continuous release of exhaled gases from the patient into the external environment. The external shape of the vent 4 includes but is not limited to circular, semi-circular and elliptical. Furthermore, the vent 4 is positioned on the surface of the second connector 24 of the elbow 2, specifically within the area that corresponds to the vertical projection along the axial line from the opening of the first connector 23. This placement ensures that the exhaust holes corresponds directly to the nasal airway, so that exhaled gas is discharged in a straight line, without the need to go through convoluted pathways or diversions, which might otherwise cause the entrapment of exhaled gases, leading to the patient re-inhaling the exhaled gas or the elbow generating unwanted noise. Such a design guarantees the smooth delivery of positive pressure gas into the patient's airway, mitigating the risk of airflow blockages and ultimately providing an optimal user experience.

Figure 6:
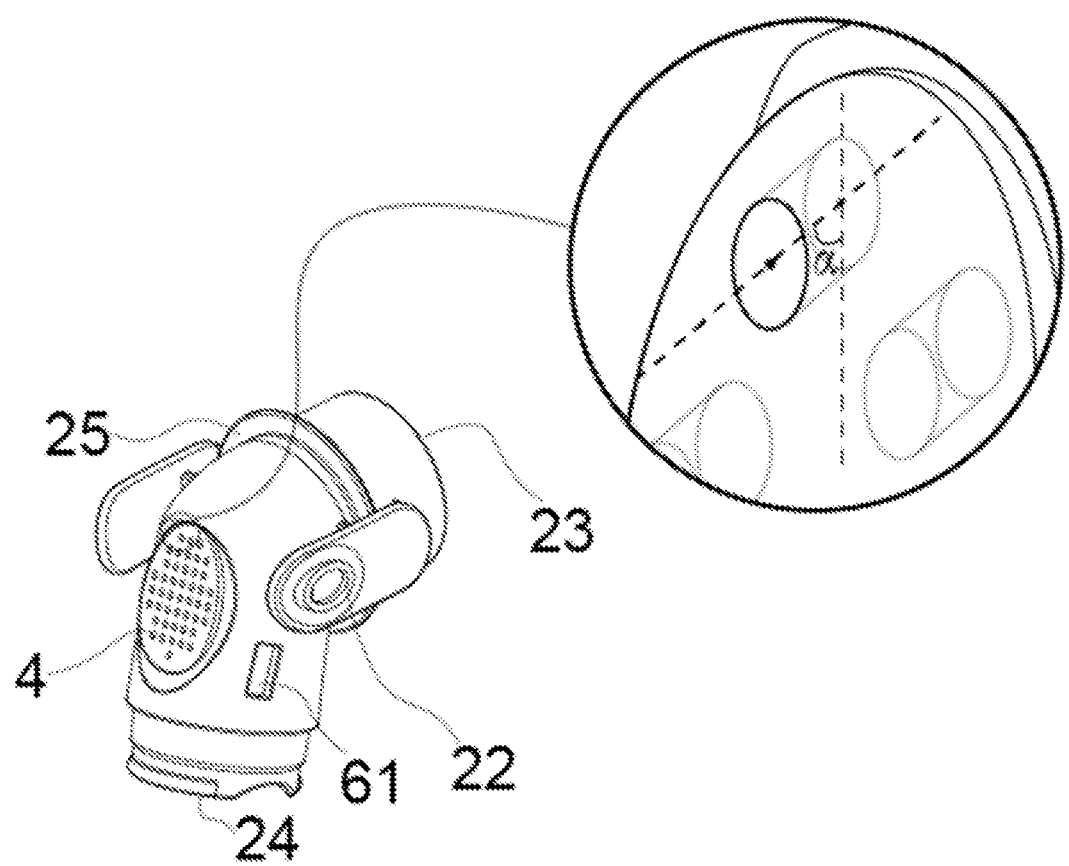
FIG. 6 is a structural schematic diagram showing the angle of the exhaust holes on the vent in the elbow of the modular elbow frame assembly for a ventilator in accordance with an example embodiment.

The vent 4 of the elbow 2 has several exhaust holes, allowing the patient's exhaled gas to pass through these holes and be released into the external environment. The total surface area of the exhaust holes is restricted to a maximum of 5 cm². Typically, under normal conditions, patients are placed on a tidal volume (the amount of air that is inhaled or exhaled from the lungs during normal breathing) of at or between 8 to 10 mL/kg, and adults exhale and inhale around 500 mL of gas with each breath. The total inner surface area or the total outer surface area of the multiple exhaust holes at the vent 4, whichever is larger, should not exceed 5 cm², given the requirements for CPAP therapy to efficiently expel the exhaled gas of the patient into the external environment. The optimal range falls at or between 0.5 to 2.5 cm². This design ensures that positive pressure gas can smoothly enter the patient's airway for respiration. Due to the change in airflow within the elbow 2, transitioning from a horizontal to a vertical direction as the airflow reaches the second connector 24, positioning the exhaust holes angled downward at a specific angle, where the axis of the exhaust holes aligns at a certain angle with the symmetrical axis of the first connector 23 of the elbow 2 is beneficial for effective gas release. This arrangement improves the expulsion of exhaled gases through the exhaust holes to the external environment. As illustrated in FIG. 6, several exhaust holes can be organized in arbitrary patterns along the elbow 2. The axis of exhaust holes is positioned at an angle α of at or between 0 to 45° concerning the symmetrical axis of the first connector 23 of the elbow 2 to guide the outflow of exhaled gas from the patient. The total external surface area of the exhaust holes accounts for at or between 3% to 50% of the external surface area of the elbow 2. And the ratio, whether calculated as the diameter of the outer interface that contacts external air divided by the diameter of the inner interface devoid of such contact, or vice versa, is less than 2.45 for at least part of the exhaust holes. In other words, the exhaust holes is conical rather than cylindrical. It could be that the diameter of the outer interface is larger than that of the inner interface, or the diameter of the inner interface is larger than that of the outer interface. This design helps to reduce the noise when the patient's exhaled gas is expelled into the external environment. However, the difference between the inner interface and the outer interface should be in an appropriate range and the ratio of their diameters should not exceed 2.45. For example, if the diameter of the inner interface is 1 mm, the maximum diameter of the outer interface should be 2.45 mm, and vice versa.

The frame 8 is configured to connect with the patient interface cushion 7, which seals the patient's airway. The frame 8 is at least partially rigid and includes a fixed opening 81 that connects to the elbow 2, a structure for detachably connecting the patient interface cushion 7 to the frame 8. The fixed opening 81 has a receiving structure 82 configured to receive the quick-release device 22 on the elbow 2. The orientation of the fixed opening 81 can vary. To ensure a stable connection between the frame 8 and the elbow 2, an adequate contact surface should be provided without compromising the wearing experience. The length of the fixed opening 81 is at or between 0.5 to 25 mm. To establish a tight fit with the first connector 23 of the elbow 2, the fixed opening has a circumference of about at or between 10 to 120 mm and a diameter of about at or between 3 to 40 mm. The shape of the fixed opening 81 can be of any regular design. The external surface area of the fixed opening 81 occupies roughly at or between 5% to 50% of the total external surface area of the frame 8. To ensure effective treatment, this proportion should be greater than 5% but less than 50%. Otherwise, airflow blockages, inadequate pressure, or airflow dispersion can occur, hindering the intended positive pressure therapy. The surface of the fixed opening 81 may include silicone material to enhance the component's airtightness.

Figure 5:
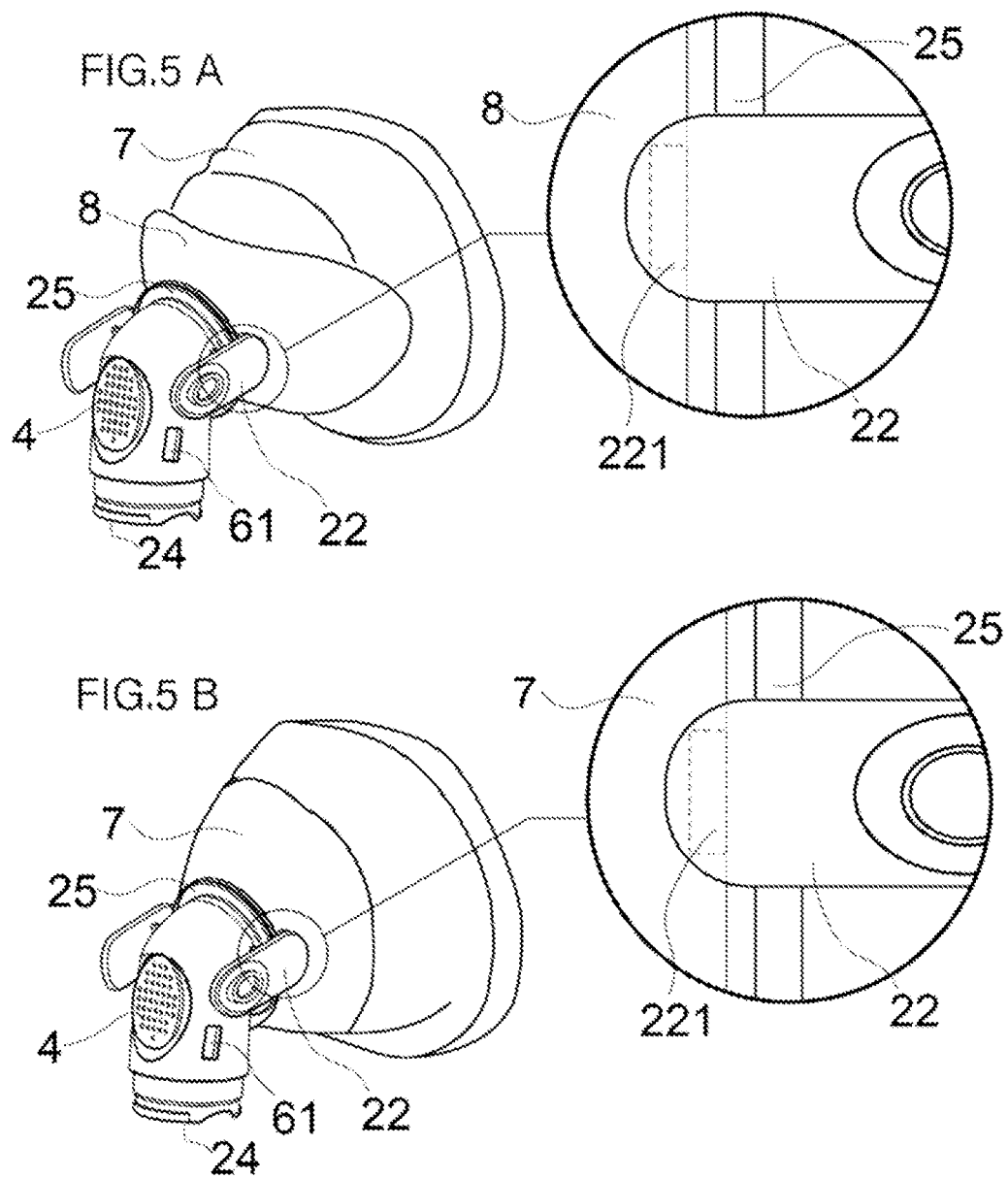
FIG. 5A and FIG. 5B are structural schematic diagrams illustrating the quick-release device in the elbow of the modular elbow frame assembly for a ventilator in accordance with an example embodiment.
Figure 16:
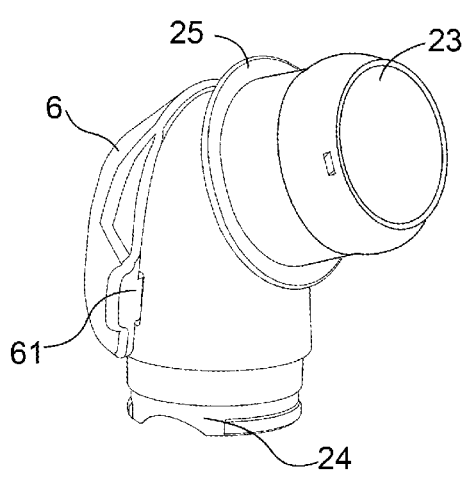
FIG. 16A and FIG. 16B are structural schematic diagrams showcasing the elbow within the modular elbow frame assembly for a ventilator without a quick-release device in accordance with example embodiments.
Figure 16:
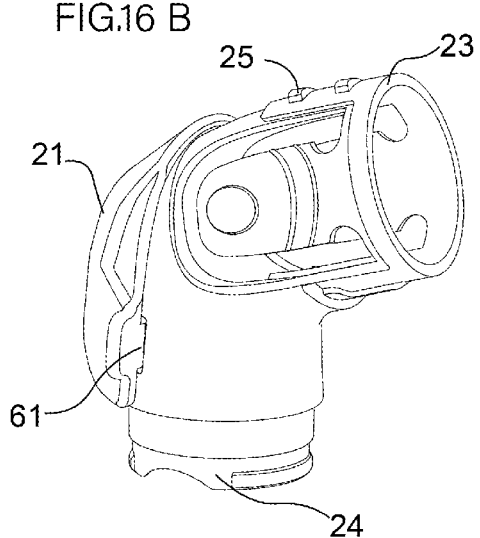

When the elbow 2 is connected to the patient interface cushion 7 or the frame 8 through the quick release device 22, in order to avoid the elbow 2 being too large in volume, the outer diameter of the first connector 23 of the elbow 2 should be less than or equal to 40 mm. As shown in FIG. 5, the quick release device 22 includes a pair of protruding pieces set on both sides of the first connector 23 and extending outward. The front ends of the protruding pieces form hook sections 221. And the patient interface cushion 7 or the frame 8 include a fixed part for attachment and coverage by the hook sections 221, with an annular positioning arm 25 on the outer edge surface of the first connector 23. The fixed part of the patient interface cushion 7 or the frame 8 embeds into the annular positioning arm 25 and the hook sections 221. In this way, the first connector 23 restricts the displacement of the fixing part in the front, back, left, and right directions, thus the patient interface cushion 7 or the frame 8 is connected to the first connector 23. Meanwhile, the axis of the first connector 23 coincides with the axis of the fixing part, allowing the first connector 23 to rotate relative to the fixing part, thereby facilitating the rotational connection between the first connector 23 and the patient interface cushion 7 or the frame 8 (FIG. 5A shows the connection between the elbow 2 and the frame 8; FIG. 5B displays the connection between the elbow 2 and the patient interface cushion 7.). The first connector 23 of the elbow 2 is integrally formed and connected with protruding pieces of the quick release device 22. In use, the elbow 2 can be attached to the patient interface cushion 7 or the frame 8 by covering the fixed part of the patient interface cushion 7 or the frame 8 with the hook sections 221 at the top of the protruding pieces. The fixed part of the patient interface cushion 7 or the frame 8 is inserted between the annular positioning arm 25 on the first connector 23 and the hook sections 221, thereby connecting the patient interface cushion 7 or the frame 8 to the elbow 2. Furthermore, the design permits relative rotation between the elbow 2 and the patient interface cushion 7 or the frame 8. In this embodiment, the quick-release device 22 includes but is not limited to a modular detachable structure which allows for the fixed part of the patient interface cushion 7 or the frame 8 to be securely inserted between the hook sections 221 at the front end of the protruding pieces and the annular positioning arm 25 on the first connector 23 by pinching the protruding pieces. An additional method involves incorporating corresponding grooves on the patient interface cushion 7 or the frame 8. Moreover, through the slight deformation (a deformation imperceptible to the naked eye when it is pressed by the patient interface cushion 7 or the frame 8 during installation) of the first connector 23 of the elbow 2, a snap-fit is engaged for a secure connection (it involves setting a protrusion at the first connector 23, which joins with a corresponding groove on the patient interface cushion 7 or the frame 8, as shown in FIG. 16). Furthermore, by integrating complementary magnets on the first connector 23 and the patient interface cushion 7 or the frame 8, a rapid detachment can be achieved.

Figure 1:
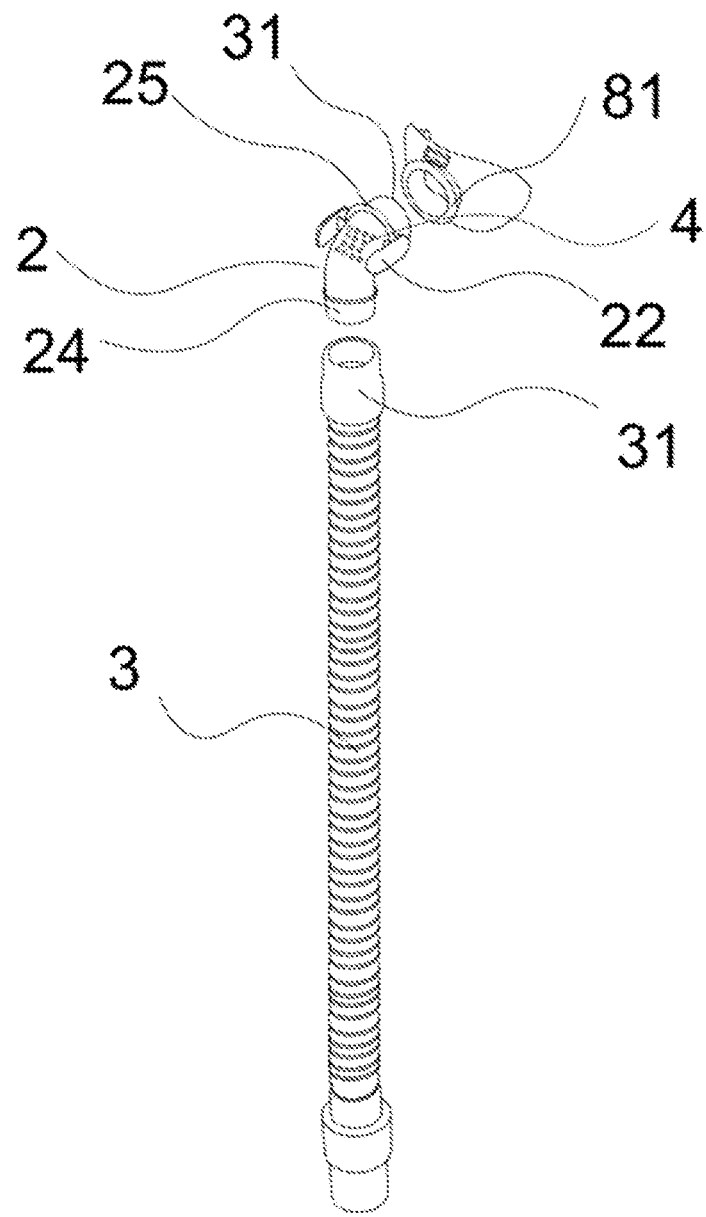
FIG. 1 is an exploded schematic diagram illustrating the modular elbow frame assembly for a ventilator in accordance with an example embodiment.
Figure 2:
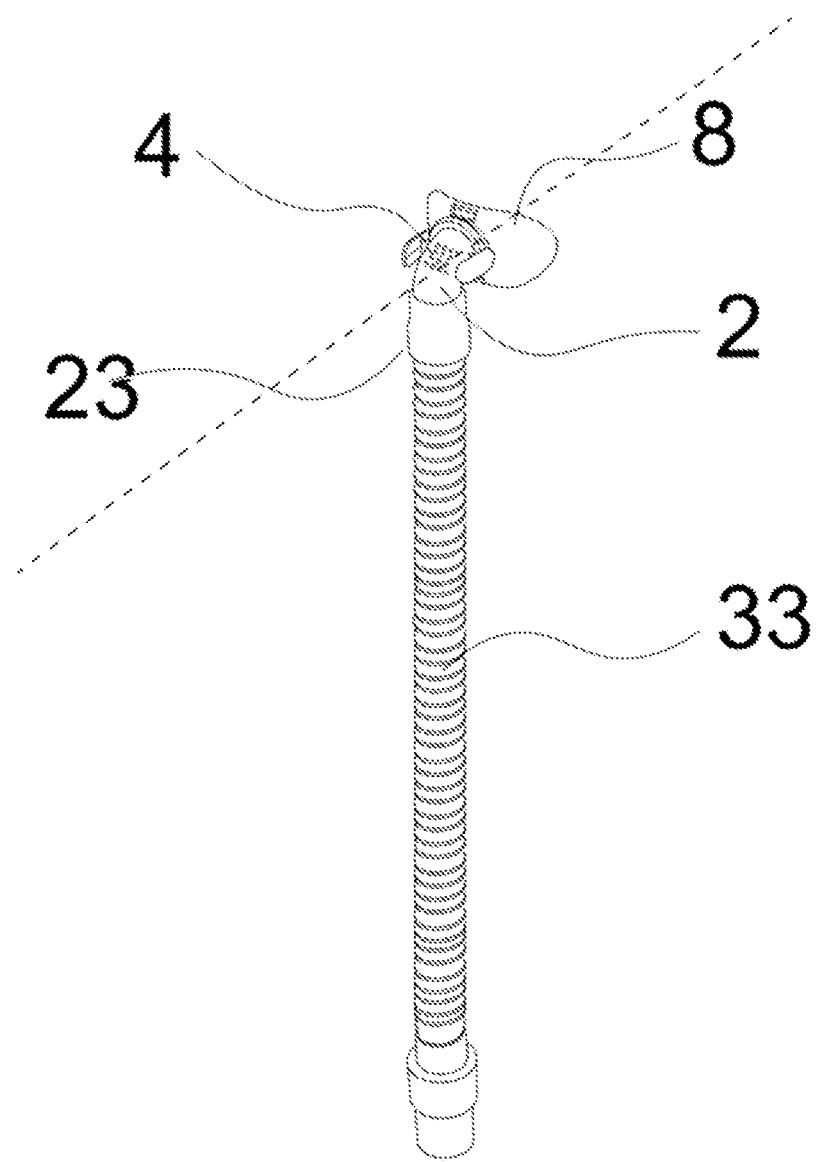
FIG. 2 is a schematic diagram illustrating the vent located on the axis of the modular elbow frame assembly for a ventilator in accordance with an example embodiment.
Figure 3:
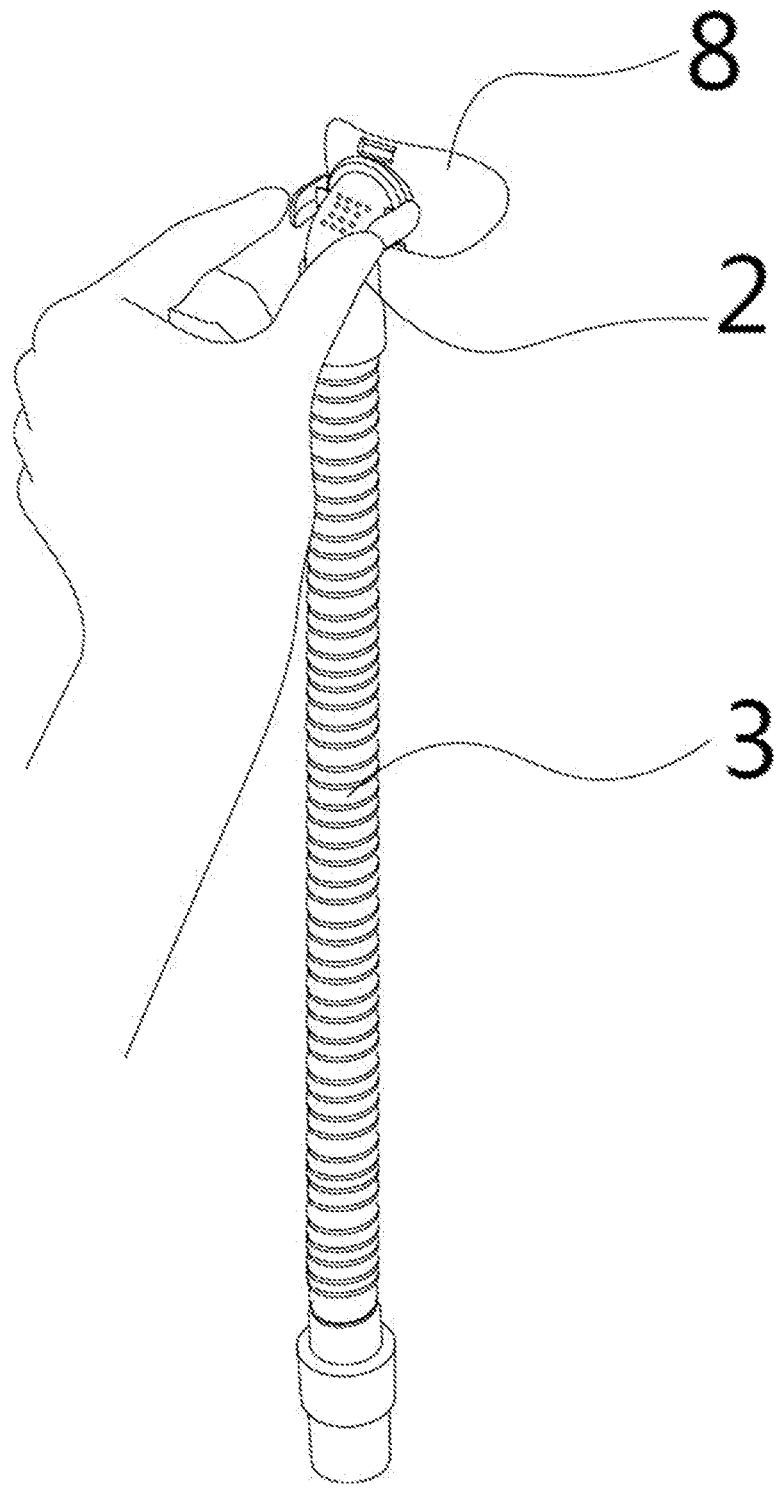
FIG. 3 is a three dimensional schematic diagram of the modular elbow frame assembly for a ventilator in accordance with an example embodiment.

As illustrated in FIG. 1 and FIG. 3, the implementation of a detachable connection between the elbow 2, the hose 3, and the patient interface cushion 7, which is affixed to a mask or nasal mask, facilitates a 360° rotation of the elbow 2 with respect to the patient interface cushion 7. This detachable design allows for swift disassembly and connection between the elbow 2 and the patient interface cushion 7 or the hose 3. This facilitates easy donning and doffing for patients and avoids complicated procedures, saving them time and effort but also delivers an overall more convenient user experience. Especially in the context of nighttime use, the quick-release feature of the elbow 2 from the patient interface cushion 7 or the hose 3 enhances the ease of wearing and removal. Patients no longer need to struggle with disassembling the equipment during nighttime awakenings, thus ensuring a smoother user experience. Furthermore, the detachable connection of the mask and the hose 3 to the elbow 2 save costs. Patients can simply replace the affected part in the event of damage, wear, or the need for the replacement of any component within the modular elbow frame assembly 1 for a ventilator, eliminating the need for the complete replacement of the entire assembly. This not only reduces replacement costs but also minimizes waste, contributing to efficient resource utilization and environmental preservation. Moreover, this design contributes to a reduction in maintenance and repair expenses. For example, when the elbow connects the hose through welding, the entire system needs to be serviced during maintenance, making the process somewhat intricate. On the contrary, the rotating feature of the elbow offers benefits to patients, as this feature allows them to adjust the mask's angle without restrictions, so that patients can opt for their preferences like sleeping positions and personal comfort. And this feature also enables patients to adjust the mask's location, ensuring a proper seal between the patient interface cushion 7 and the airway. Furthermore, fixed and knotted hoses can introduce various risks, including treatment interruptions, obstructed breathing, and discomfort during use. These risks not only make the operation of the treatment equipment more complex but can also lead to patient fatigue and reluctance to continue using the treatment equipment when the risks occur frequently. In contrast, with a rotational feature, the tangling between the frame 8 and the hose 3 can be avoided. This feature helps reduce the occurrence of hose entanglement and extends the durability of the hose 3.

Figure 10:
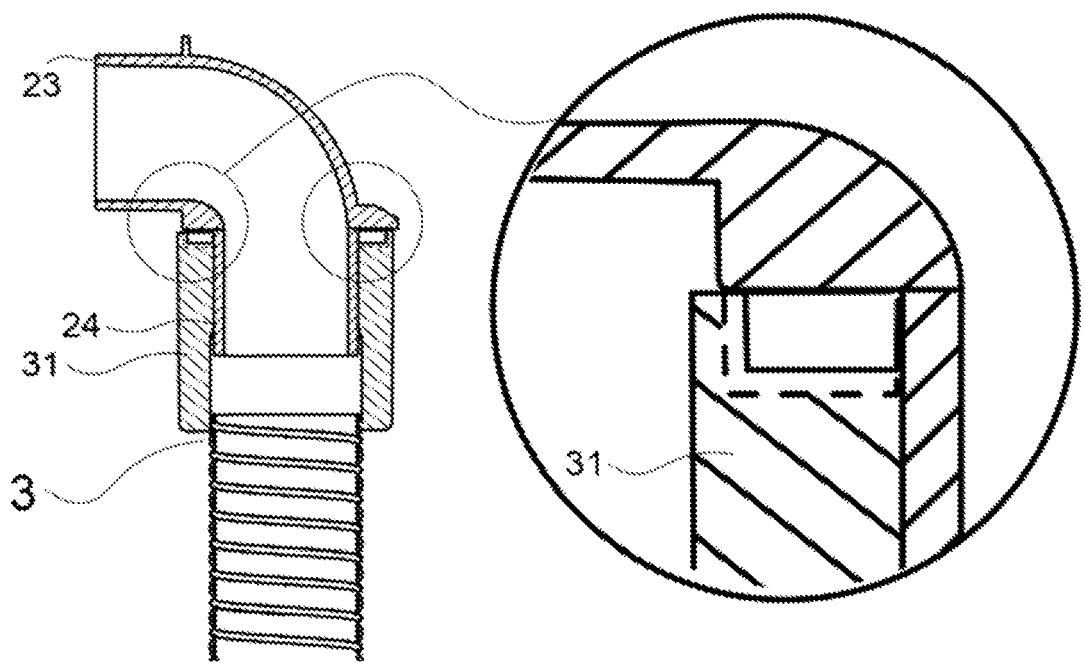
FIG. 10 is a schematic diagram illustrating the adsorptive connection between the hose and the elbow in the modular elbow frame assembly for a ventilator in accordance with an example embodiment.

The hose 3 has a first end 31 close to or nearer the elbow 2, a second end 33 away from the elbow 2, a spiral tube situated between the first end 31 and the second end 33, consisting of several adjacent coils. The hose 3 is detachably connected to the elbow via the first end 31 and the gas pressurized by the ventilator is then channelled into the patient's airway. The elbow 2 and the first end 31 of the hose 3 is detachably connected through a snap-fit connection. The second end 33 of the hose 3 connects to the ventilator tube, and a rotating component is configured on the second end 33 of the hose 3, providing a rotational connection between the hose 3 and the ventilator tube. The first connector 23 of the elbow 2 has an outer diameter of at or between 10 to 40 mm, and the second connector 24 has a similar outer diameter of at or between 10 to 40 mm. When the second connector 24 of the elbow 2 is connected to the hose 3, considering the comfort of patients, the hose 3 is typically light and thin. However, to ensure effective airflow, the inner diameter of the hose 3 is equal to or greater than 10 mm, the outer diameter of the second connector 24 of the elbow 2 connected to the hose 3 is also equal to or greater than 10 mm. The detachable design between the first end 31 of the hose 3 and the elbow 2, facilitated by a snap-fit connection, allows for the connection between the elbow 2 and the hose 3 to create an airflow pathway. In this way, the pressurized gas generated by the ventilator can flow smoothly through the hose 3, pass through the elbow 2 and then enter into the patient's airway for respiration. Additionally, this design allows for quick detachment and assembly between the elbow 2 and the hose 3, which facilitates the quick replacement of the hose 3 and the elbow 2, meeting different requirements for patients. Furthermore, a rotating component enables a rotational connection between the second end 33 of the hose 3 and the ventilator tube. This feature improves patients' range of motion and prevents the hose 3 from tangling, thus providing a better experience for patients. Consequently, this design prolongs the lifespan of the hose 3. As depicted in FIG. 10, a magnetic attachment can also be employed to connect the first end 31 of the hose 3 and the elbow 2. Both the second connector 24 of the elbow 2 and the first end 31 of the hose 3 have complementary magnets. This magnetic connection ensures stability in the connection between the elbow 2 and the hose 3 while enhancing the ease of detachable connection between the elbow 2 and the hose 3.

Figure 24:
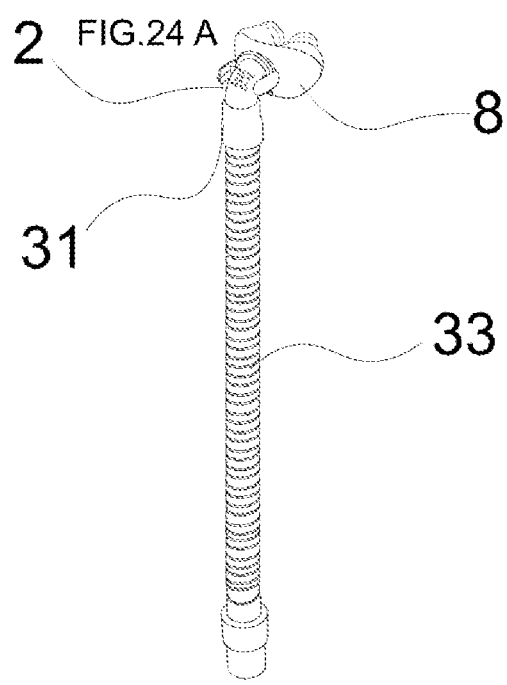
FIG. 24A and FIG. 24B are schematic diagrams depicting the frame connected to different nasal masks of the modular elbow frame assembly for a ventilator in accordance with an example embodiment.
Figure 24:
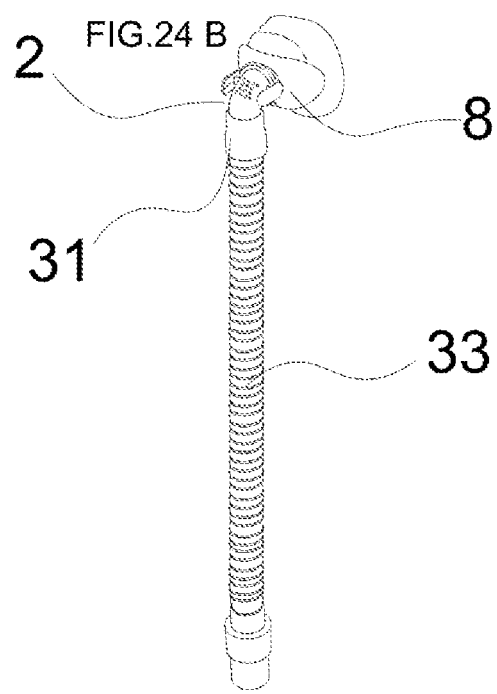

In some other embodiments, the modular elbow frame assembly 1 for a ventilator, in addition to connecting with a face mask, can also be connected to patient interface cushions such as a nasal pillow, a nasal mask, and the like (as shown in FIG. 24, FIG. 24A is a nasal pillow interface and FIG. 24B is a nasal mask interface). By detachably connecting a frame 8 with a face mask, a nasal mask, or a nasal pillow to the first connector 23 of the elbow 2, the face mask, the nasal mask, or the nasal pillow that fits against the patient's face has been made more flexible and adaptable. Moreover, patients have the option to select from various cushion types like face masks, nasal masks, or nasal pillows that are tailored to their specific needs, whether it be treatment needs or personal comfort preferences. The flexible nature of face masks, nasal masks, or nasal pillows allows patients to make personalized adjustments, enhancing the overall effectiveness of the treatment and delivering a more comfortable experience for patients.

Embodiment 2

As illustrated in FIG. 11 to FIG. 15, this embodiment presents a modular elbow frame assembly 1 for a ventilator, configured for delivering positive pressure gas to a patient's airway. The modular elbow frame assembly 1 for a ventilator includes a hose 3, a frame 8, an elbow 2, an external connecting component 21, and a quick-release device 22. This embodiment includes schematic diagrams, an exploded schematic diagram, and a cross-sectional schematic diagram of the modular elbow frame assembly 1 for a ventilator. In this embodiment, as demonstrated in FIG. 11 to FIG. 15, there are distinctions from a modular elbow frame assembly 1 for a ventilator in Embodiment 1: the modular elbow frame assembly 1 for a ventilator incorporates an external connecting component 21. The external connecting component 21 includes a noise reduction element 41 internally. And the external connecting component 21 can include a main body for detachably connecting to the elbow 2 and an opening 6 set at the center of the main body to accommodate the noise reduction element 41. The main body has snap buckles 61 on both sides which are snap-fittable onto the retaining component on the elbow 2.

Figure 14:
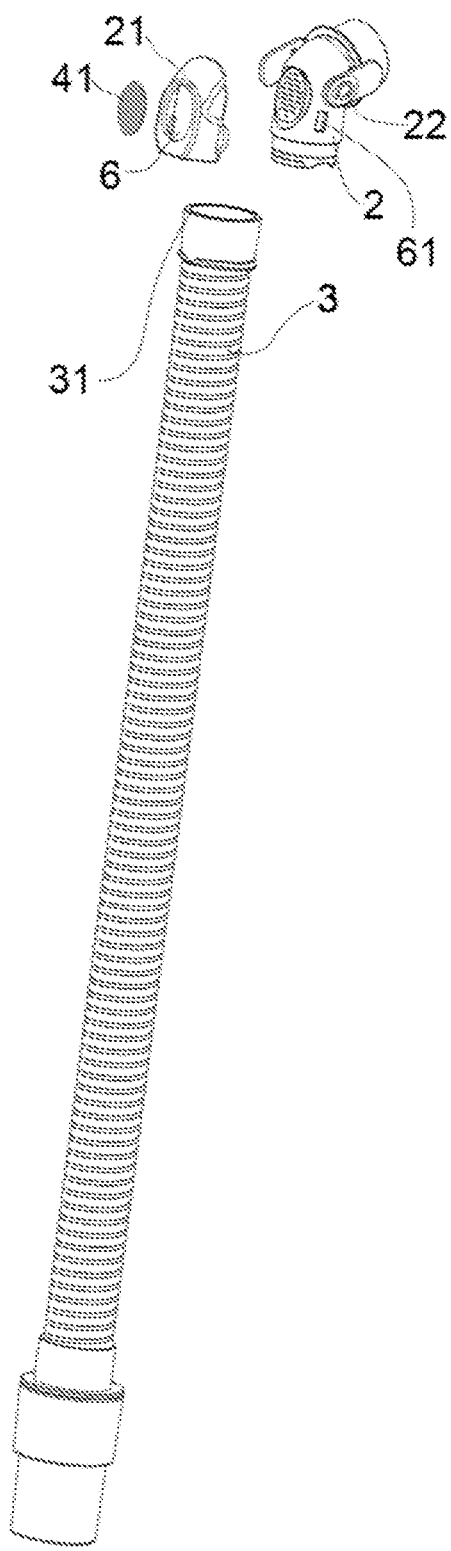
FIG. 14 is another exploded schematic diagram illustrating the modular elbow frame assembly for a ventilator in accordance with an example embodiment.
Figure 15:
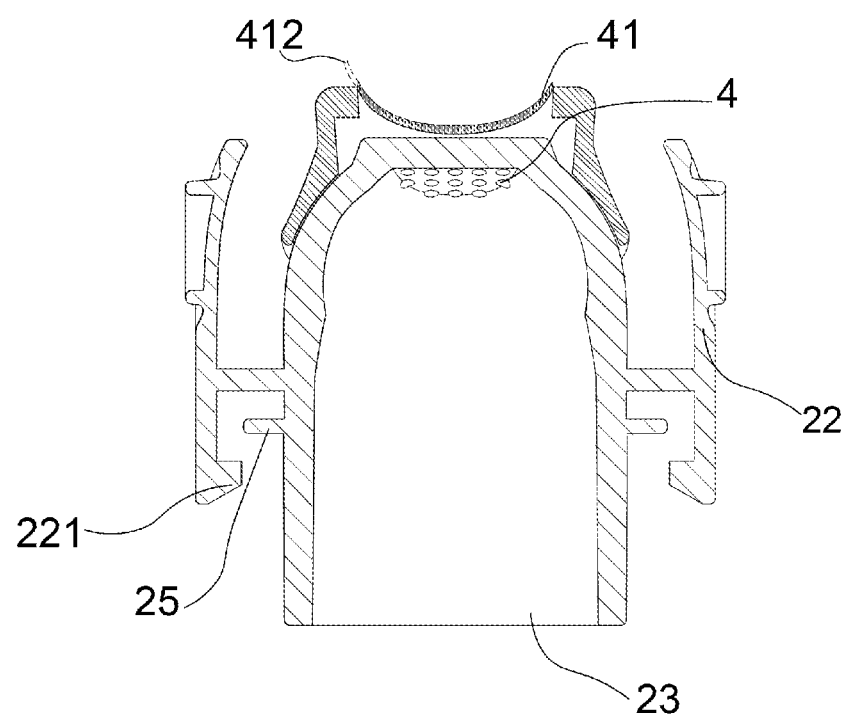
FIG. 15 is a cross-sectional schematic diagram taken along line A-A in FIG. 12.

As illustrated in FIG. 14, the elbow assembly can include one or more external connecting components 21 for connection to the elbow 2. The external connecting components 21 has the capacity to house a noise reduction element 41. To strike a balance between noise reduction and overall component weight, the noise reduction element 41 is limited to a weight of no more than 7 g and a maximum thickness of 9 mm. The noise reduction element 41 can be positioned on the outer surface of exhaust holes of the elbow 2, configured for the continuous dispersion of exhaled gas from the patient into the external environment. This design contributes to noise reduction and minimizes the possibility of the patient re-breathing exhaled carbon dioxide.

An external connecting component 21 has a retaining component for attachment to the outer surface of the elbow 2. The external connecting component 21 includes a main body that connects to the elbow 2 and a noise reduction element 41 affixed to the main body. The external connecting component 21 incorporates at least one exhaust opening, which can be various shapes, such as circular, arc-shaped, semi-circular, or other symmetric or asymmetric forms. The outer surface of the elbow 2 features at least one corresponding component that interacts with the retaining component on the external connecting component 21. Both the retaining component and the corresponding component can be configured with other suitable shapes (such as cylindrical, square) for connection to facilitate the secure placement of the noise reduction element 41 and effective gas dispersion. Moreover, the external connecting component 21 and the noise reduction element 41 can be fixedly connected through methods, including injection molding, ultrasonic bonding, heat pressing, or the use of adhesive materials such as glue and tape, or be detachably connected through fastening mechanisms such as a snap-fit connection, a knob, or a clip, providing patients with diverse options to cater to the usage needs of different patients.

In this embodiment, the noise reduction element 41 can be made of a variety of materials, including but not limited to noise reduction cotton and noise reduction mesh. The noise reduction materials consist of fibrous sound-absorbing materials, foam sound-absorbing materials, or other suitable options. The noise reduction mesh (made of metal, fiber, or other flexible or ductile materials interwoven together, with many interwoven threads forming spaced holes) can be composed of fabrics, nylon, polypropylene, or alternative materials. The exhaust opening of the external connecting component 21, located in the middle part relative to the periphery, has at least an opening 6 with or without a taper. The noise reduction element 41, connected to the external connecting component 21 and positioned within the opening 6, includes a central part and an outer edge portion. Being appropriately sized and placed within the opening 6 of the external connecting component 21, when connected to the elbow 2, the noise reduction element 41 is attached to the outer surface of the vent 4 of the elbow 2 through which exhaled gas disperses into the external environment. The perimeter of the edge of the noise reduction element 41 is greater than the inner wall perimeter of the opening 6 of the external connecting component 21. During use, the noise reduction element 41 and the external connecting component 21 are securely coupled to work together, with the noise reduction element 41 being positioned to remain between the vent 4 of the elbow 2 and the external connecting component 21. Besides, the opening 6 of the external connecting component 21 has an area of no more than 5 $cm^2$ to accommodate the noise reduction element 41 with a certain surface area.

Figure 11:
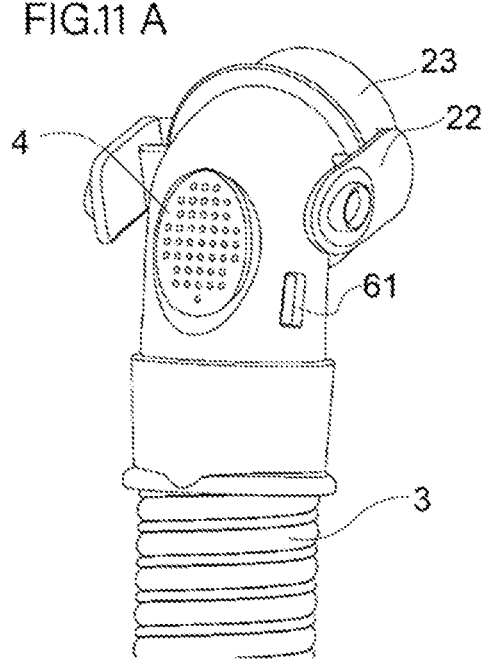
FIG. 11A and FIG. 11B are structural schematic diagrams showing the modular elbow frame assembly for a ventilator with or without an external connecting component in accordance with an example embodiment.
Figure 11:
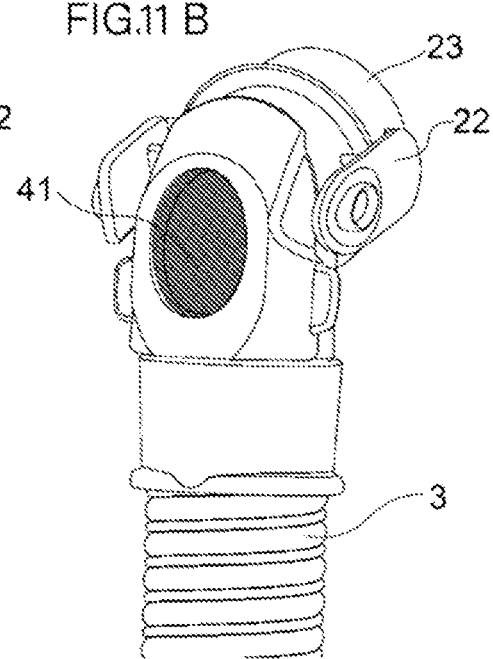
Figure 12:
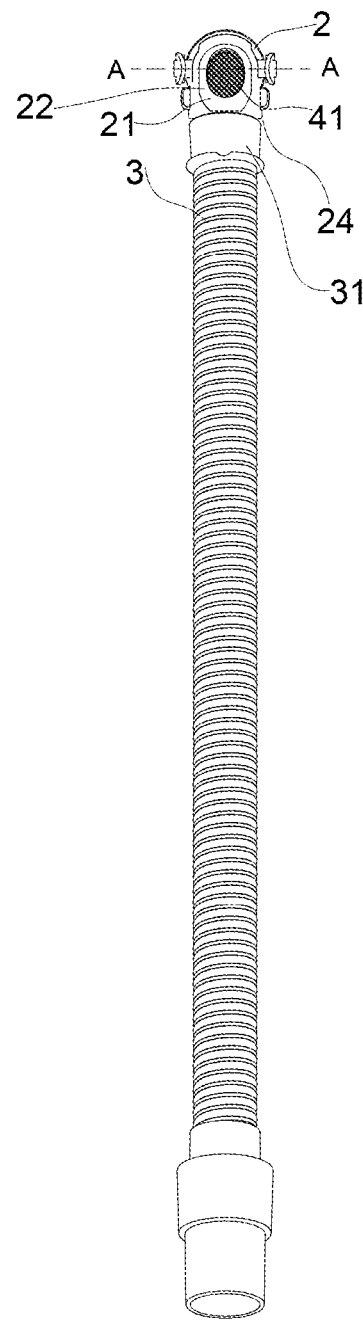
FIG. 12 is a front view of the modular elbow frame assembly for a ventilator in accordance with an example embodiment.
Figure 13:
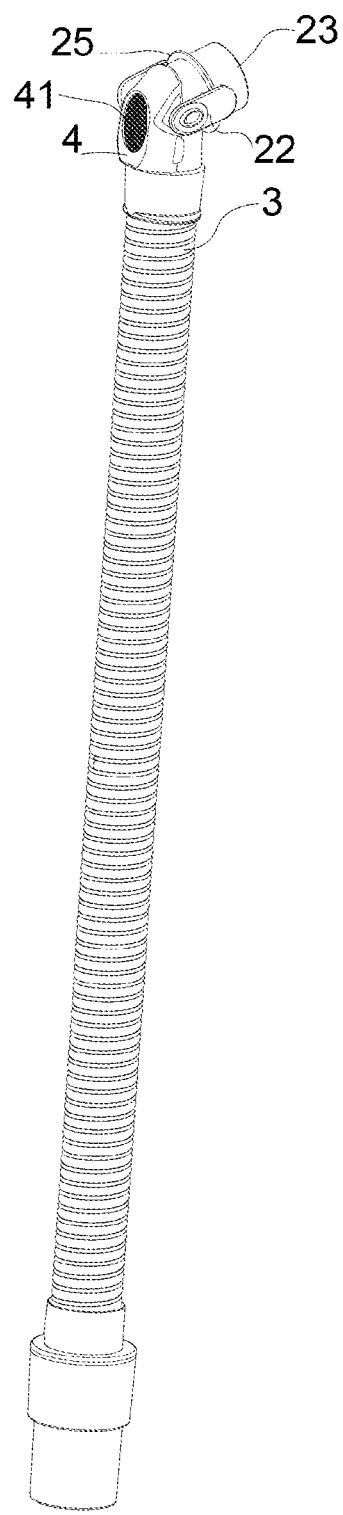
FIG. 13 is a three dimensional structural schematic diagram of the modular elbow frame assembly for a ventilator in accordance with an example embodiment.

Patients have varying preferences regarding noise reduction design. Offering two variations of the fixed elbow, one with noise reduction cotton and one without, may present certain challenges for patients when making their choices. However, by implementing a detachable design for the external connecting component 21 on the elbow 2, patients can make their selections freely as shown in FIG. 11. They can choose to install the noise reduction element 41 (illustrated in FIG. 11B). or leave the noise reduction element 41 out entirely (illustrated in FIG. 11A). This design offers flexibility, allowing patients who prefer not to use the noise reduction element 41 to easily detach or ensuring easy replacement of the noise reduction element 41 in case of damage. This not only enhances the component's lifespan but also facilitates cleaning. Furthermore, the noise reduction material can also be replaced. Patients can opt for different noise reduction effects and experiences by selecting noise reduction elements 41 with noise reduction cotton or noise reduction mesh. The detachable design also addresses the issues of hard-to-reach areas that make cleaning difficult for patients and the non-replaceability of the existing non-detachable products.

In other embodiments, the elbow 2 of the elbow frame assembly 1 for a ventilator can establish a connection with the patient interface cushion 7 or the frame 8 using through a round ball-shaped interface or a straightforward snap-fit mechanism (as illustrated in FIG. 16). With a round ball-shaped interface (as shown in FIG. 16A) or a snap-fit mechanism (as shown in FIG. 16B) that can be inwardly pinched at the first connector 23 of the elbow 2, the elbow 2 is connected to the patient interface cushion 7 or the frame 8. To ensure smooth airflow transmission when the elbow 2 is connected to the patient interface cushion 7 or the frame 8, the outer diameter of the first connector 23 of the elbow 2 should be equal to or greater than 10 mm. The length of the quick-release device 22 can be at or between 0.5 to 35 mm. The quick-release device 22 can assume different forms, with the smallest being a small protrusion on the first connector 23 of the elbow 2, configured to snap firmly into place within the patient interface cushion 7 or the frame 8. The height of this protrusion should be a minimum of 0.5 mm. The largest form could involve an extension of a particular section of the elbow 2 (as depicted in FIG. 11 as the quick-release device 22). To ensure user comfort, taking into account thumb width and the overall weight of the elbow 2, the length of this extension should not exceed 35 mm. By using different joining methods between the elbow 2 and the patient interface cushion 7 or the frame 8, the diversity of combinations between the elbow 2 and the patient interface cushion 7 or the frame 8 are increased, thereby enhancing the range of choices available to patients.

Figure 25:
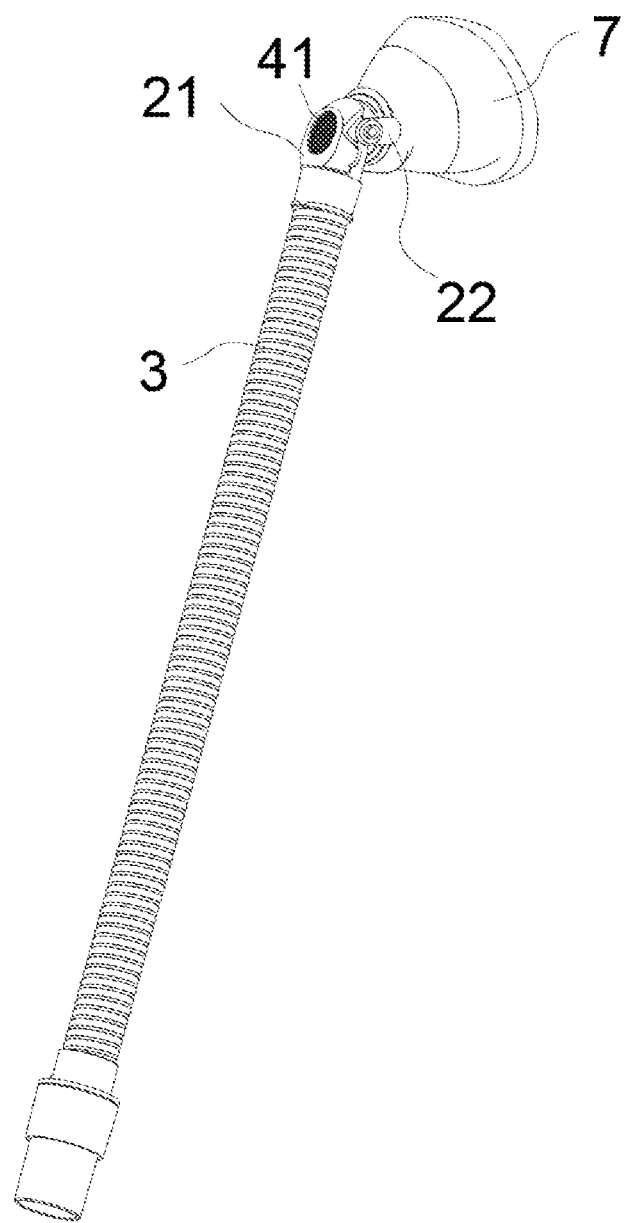
FIG. 25 is a structural schematic diagram illustrating the connection between the elbow and the nasal mask in the modular elbow frame assembly for a ventilator in accordance with an example embodiment.

In some other embodiments, the modular elbow frame assembly 1 for a ventilator can also establish connections not only with face masks but also with nasal pillows, nasal masks, or other types of patient interface cushions (as illustrated in FIG. 25).

Embodiment 3

Figure 20:
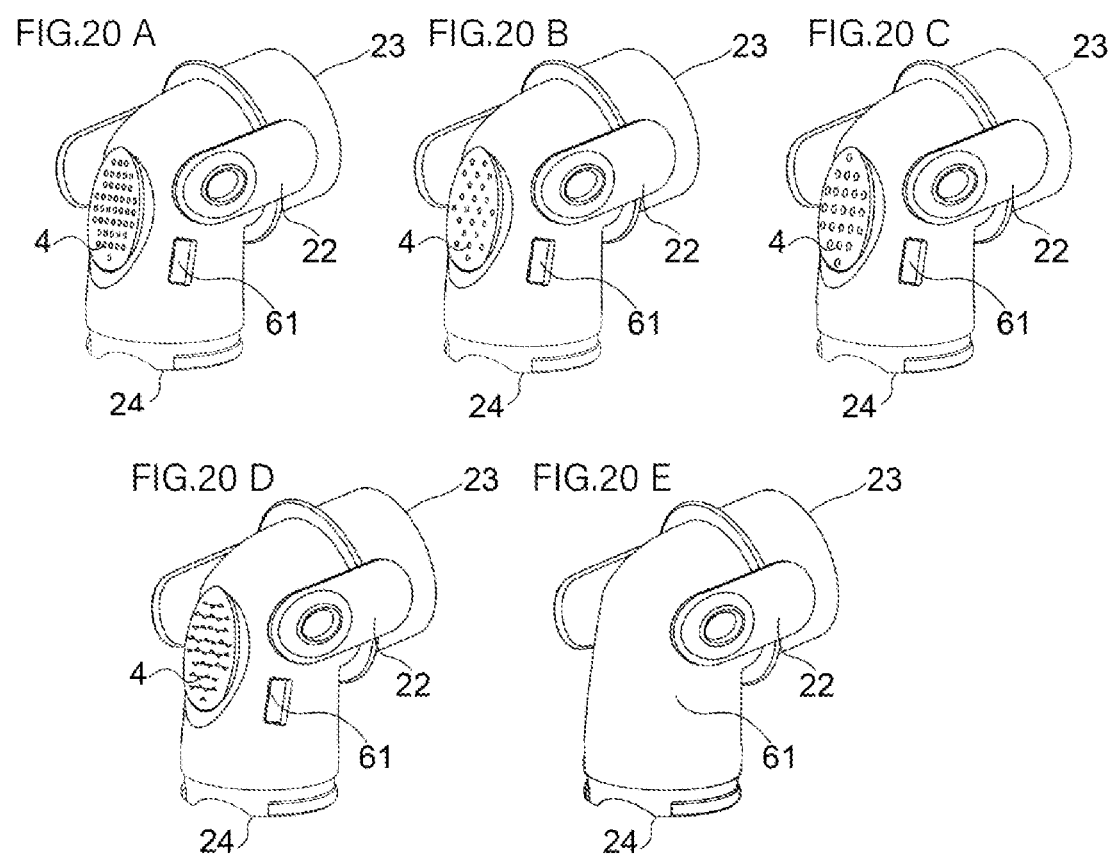
FIG. 20A, FIG. 20B, FIG. 20C, FIG. 20D, and FIG. 20E are structural schematic diagrams showcasing the elbow with different vents of the modular elbow frame assembly for a ventilator in accordance with an example embodiment.

As shown in FIG. 20, this embodiment provides structural schematic diagrams of different vents 4 on the elbow 2 of a modular elbow frame assembly 1 for a ventilator, configured to deliver positive pressure breathing gas to a patient's airway. The modular elbow frame assembly 1 for a ventilator includes a hose 3, a frame 8, an elbow 2, and a quick-release device 22. In this embodiment of the disclosure, depicted in FIG. 20, a distinction from the Embodiment 1 of the elbow frame assembly 1 for a ventilator is as follows: several exhaust holes can be arranged on the elbow 2 in any desired pattern, and these exhaust holes can be of different numbers, diameters, and shapes at the vent 4 of the elbow 2, which caters to the needs of different patients regarding airflow pressure. The elbow 2 is configured to be modular and detachable, enabling healthcare providers to interchange different elbows 2 to connect with the hose 3 based on the requirements of various patients. When a patient does not receive the optimal airflow pressure from the ventilator, they can adjust the airflow pressure entering the patient's airway by replacing the elbow 2 with different configurations of exhaust holes, including variations in diameter and number. Different patients have varying needs for the pressure and airflow entering their airways. Therefore, the elbow 2 has different numbers, diameters, and shapes of exhaust holes, and this modular design of the elbow assembly allows patients to choose elbow configurations that best suit their needs, thereby enhancing the comfort of continuous positive airway pressure (CPAP) therapy. The modular detachable design of the elbow gives patients more choices and allows patients to select an elbow 2 with exhaust holes of different numbers or diameters tailored to their personal airway resistance, which helps them to choose a suitable elbow 2 to optimize their CPAP therapy experience. (It's important to note that the greater the number and the diameter of exhaust holes, the larger the total opening area of the exhaust holes, which results in lower received airflow pressure for the patient.) Furthermore, exhaust holes of different shapes have varying effects on air dispersion. By adjusting the shape of these holes (such as circular, elliptical, diamond, triangular), the diverse needs of individual patients concerning airflow pressure can be met. For patients with respiratory insufficiency and respiratory failure, there is an option to use the elbow 2 without exhaust holes. In addition, to ensure patient comfort when using various components, the weight of the elbow 2 should not exceed 20 g. Otherwise, the elbow would bring significant discomfort for the patient, exceeding an acceptable threshold of patient weight-bearing. Therefore, to guarantee the comfort of patients, the weight of the elbow 2 should be configured to be within 20 g.

Embodiment 4

Figure 17:
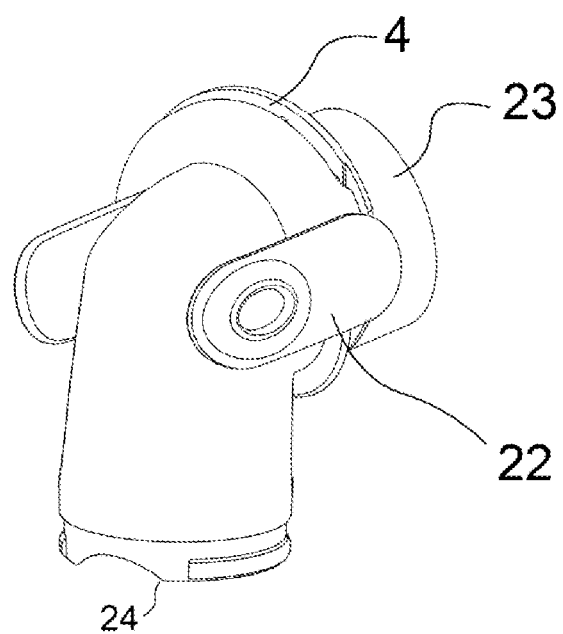
FIG. 17 is a structural schematic diagram illustrating the elbow with the vent set at the first connector in the modular elbow frame assembly for a ventilator in accordance with an example embodiment.
Figure 18:
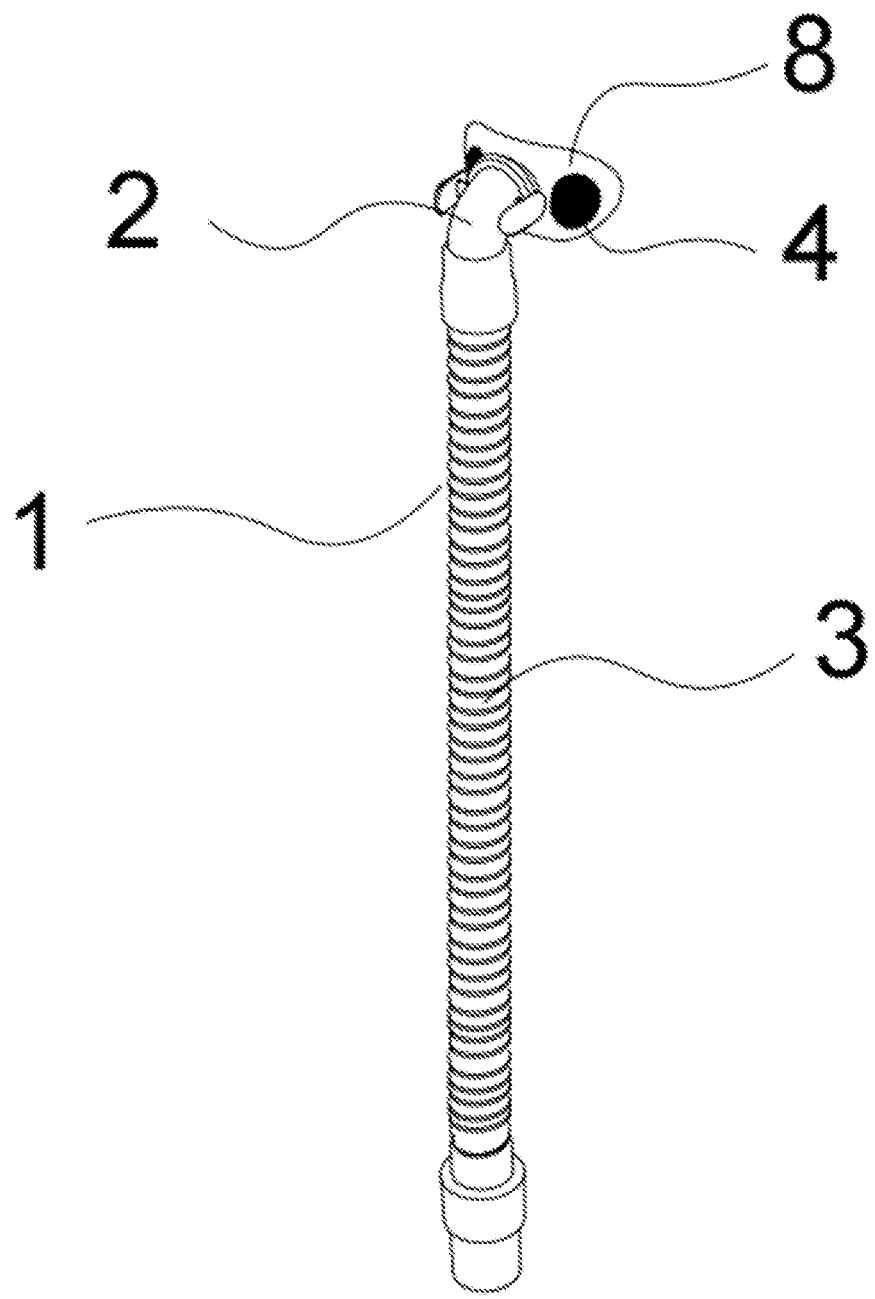
FIG. 18 is a schematic diagram depicting the vent located on the frame of the modular elbow frame assembly for a ventilator in accordance with an example embodiment.
Figure 19:
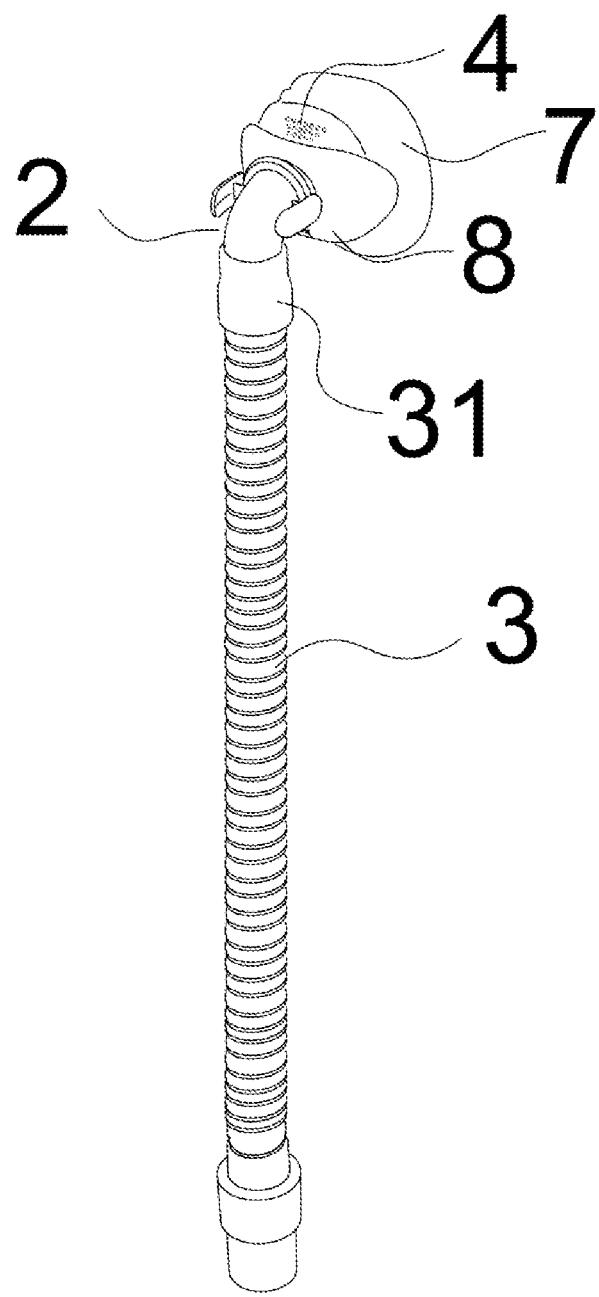
FIG. 19 is a schematic diagram illustrating the vent positioned on the patient interface cushion of the modular elbow frame assembly for a ventilator in accordance with an example embodiment.

In FIGS. 17 through 19, this embodiment presents a structural schematic diagram of vents 4 with different positions on a modular elbow frame assembly 1 for a ventilator, configured to deliver positive pressure breathing gas to a patient's airway. The modular elbow frame assembly 1 for a ventilator has a hose 3, a frame 8, an elbow 2, a quick-release device 22, as well as an external connecting component 21. This embodiment presents a structural schematic diagram of modular elbow frame assembly 1 for a ventilator. In the embodiments in FIGS. 17 through 19, as compared to Embodiment 1 of the elbow frame assembly 1 for a ventilator, a notable distinction lies in the placement of the vent 4, which can also be located on the frame 8 as illustrated in FIG. 18. The vent 4 can be configured as exhaust grids utilizing noise reduction elements 41, or alternatively, they can include several exhaust holes that directly traverse the frame 8. The vent 4 is configured to allow the discharge of exhaled gas from within the frame 8 to the external environment. The shape of the vents 4 can be, but not limited to, circular, semi-circular, or elliptical forms. The exhaust holes can be arranged on the frame 8 in arbitrary patterns. Moreover, mesh-style vents 4 can be positioned at any location on the surface of the frame 8 and the shape can be symmetrical or asymmetrical with their surface area typically accounting for at or between 3% to 90% of that of the frame 8. This design facilitates a constant and uniform gas outflow, mitigating airflow blockages. The exhaust holes on the frame 8 can be applied in conjunction with an external connecting component 21 for noise reduction, which means that interfaces for affixing the external connecting component 21 can be integrated into the corresponding components, or the external connecting component 21 itself can form a fixed structure. The vent 4 can be made of, but is not limited to, materials such as polyvinyl chloride, polypropylene, polycarbonate, polytetrafluoroethylene, or nylon, among others. The external connecting component 21 includes noise reduction cotton which can be made of one or more materials, including but not limited to materials like polyester, polypropylene, nylon, vinyl, and natural fabrics.

In another embodiment, the vent 4 can also be placed on the patient interface cushion 7 (as shown in FIG. 19). In another embodiment, besides being placed on the wall of the elbow 2 close to the second connector 24, the vent 4 can also be set near the first connector 23 (as shown in FIG. 17). Given the limited placement options for the vent 4 on elbows available on the current market, positioning the vent 4 closer to the interface of the first connector 23 offers patients more choices. This further allows patients to choose an elbow 2 with exhaust holes of different numbers or diameters, as well as the location of the vent 4, based on their personal airway resistance. This enhances the comfort of CPAP therapy and improves the patient's overall experience.

Embodiment 5

Figure 21:
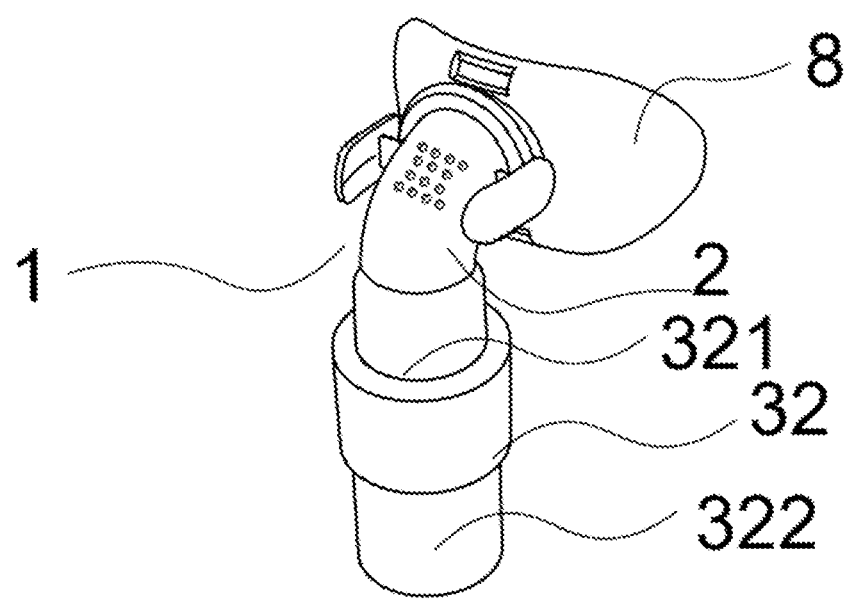
FIG. 21 is a schematic diagram showing the vent set on the elbow of the modular elbow frame assembly for a ventilator in accordance with an example embodiment.
Figure 22:
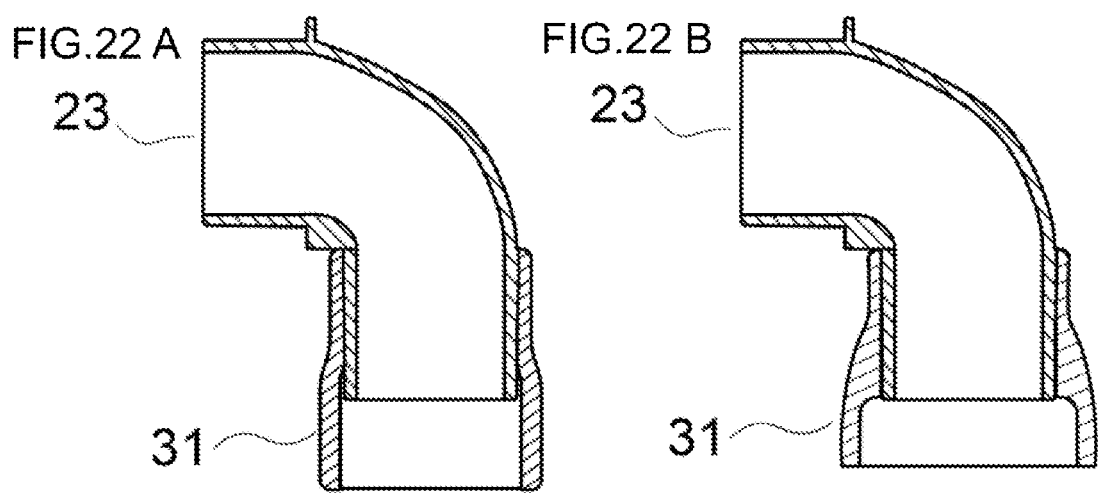
FIG. 22A and FIG. 22B are schematic diagrams illustrating the connection between the elbow and the ventilator tube of the modular elbow frame assembly for a ventilator in accordance with an example embodiment.
Figure 23:
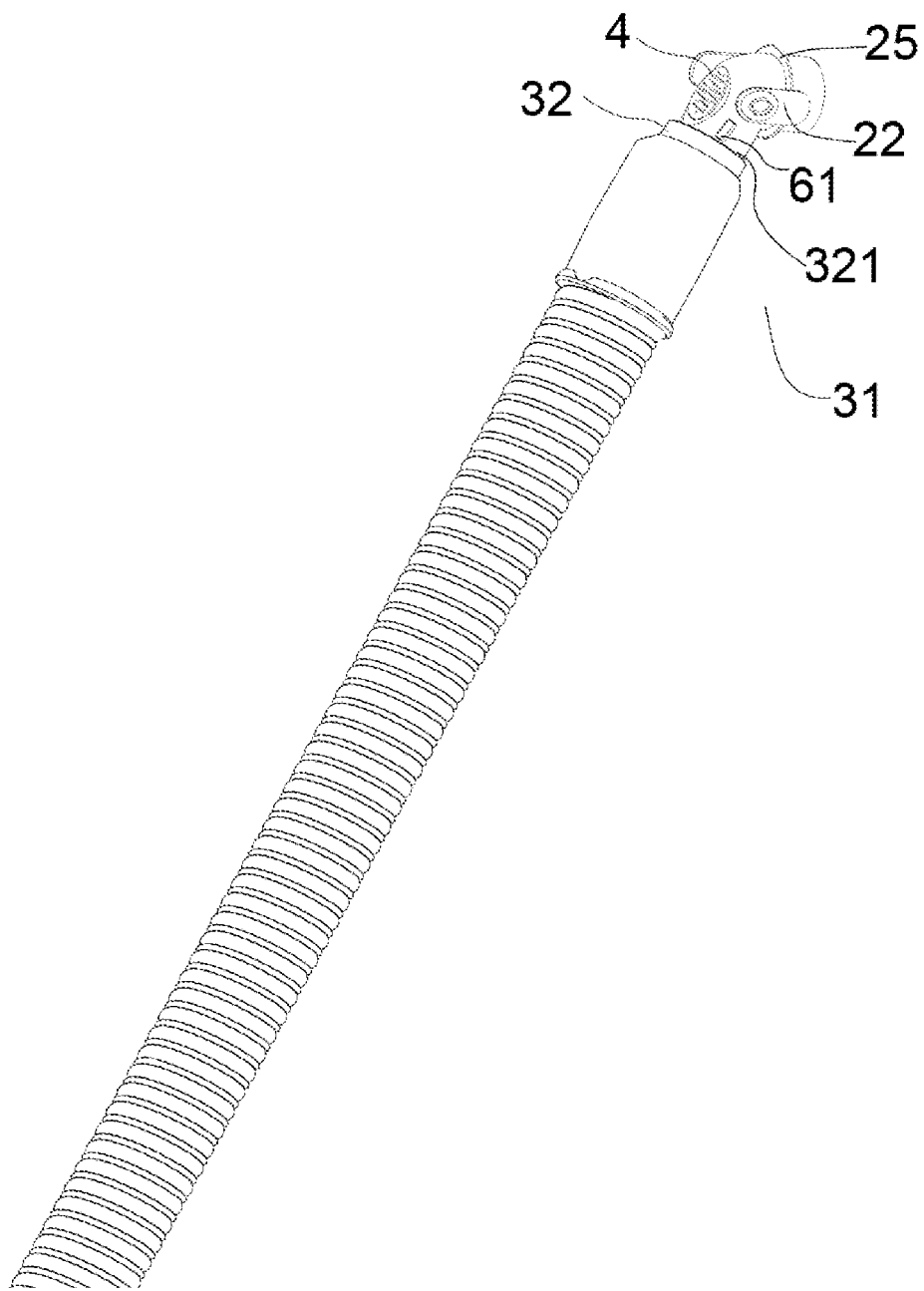
FIG. 23 is a structural schematic diagram showing the elbow connected to the ventilator tube through a tubular connector in the modular elbow frame assembly for a ventilator in accordance with an example embodiment.

As shown in FIG. 21 to FIG. 23, this embodiment provides schematic diagrams of a modular elbow frame assembly 1 for a ventilator, which includes a tubular connector 32. It is configured to deliver positive pressure breathing gas to a patient's airway. The modular elbow frame assembly 1 for a ventilator includes a frame 8, an elbow 2, a quick-release device 22, and a tubular connector 32. This embodiment provides structural schematic diagrams of the modular elbow frame assembly 1 for a ventilator, a detailed sectional schematic diagram of the connections (FIG. 22A shows the connection of the elbow 2 with a tubular connector 32 at a 15 mm outer diameter and FIG. 22B displays the connection of the elbow 2 with a tubular connector 32 at a 22 mm outer diameter), and a schematic diagram of the connection effects. In this embodiment of the disclosure in FIG. 21 to FIG. 23, the elbow 2 is the same as Embodiment 3, and is different from the modular elbow frame assembly 1 for a ventilator in Embodiment 1, in that the modular elbow frame assembly 1 for a ventilator has a tubular connector 32 for connecting the elbow 2 to the ventilator tube. The tubular connector 32 includes a second port 322 connected to the ventilator tube and a first port 321 connected to the elbow 2. It is constructed to form a releasable connection with both the elbow 2 and the ventilator tube. The connection between the second connector 24 of the elbow 2 and the second port 322 of the tubular connector 32 includes, but is not limited to, a connection method using a snap-fit structure fixed by a protrusion or groove on one end and a buckle on the other end, a method of detachably connecting the tubular connector 32 to the second connector 24 through a mechanical structure for pinch-and-release operation, and a magnetic attraction method using complementary positive and negative poles on the tubular connector 32 and the elbow 2.

As shown in FIG. 23, the second port 322 of the tubular connector 32 is configured to connect to conduits such as ventilator tubes (heated tubes, breathing tubes) for the transmission of gases. And the cross-sectional shape of the front end of the tubular connector 32 is configured to match the second connector 24 of the elbow 2 with its overall length at or between 5 to 60 mm. The tubular connector 32 is made from one or more materials, including but not limited to polycarbonate, polyethylene, polypropylene, silicone, thermoplastic elastomer, and others.

As shown in FIG. 22, the second port 322 of the tubular connector 32, which is connected to the ventilator tube, is configured to have at least a portion that makes contact with the ventilator tube, accommodating ports with diameters of either 22 mm or 15 mm. When the second connector 24 is connected to the tubular connector 32, the tubular connector 32 is typically used in conjunction with larger tubing, such as heated tubes and breathing tubes. The inner diameter of such tubing connectors is either 15 mm or 22 mm, and their outer diameter is about at or between 20 to 30 mm. The connecting section of the tubular connector 32 which attaches to these tubes is a uniform cylinder, resulting in an outer diameter at or between 15 to 22.5 mm. The outer diameter of the second connect 24 of the elbow 2, which connects to the tubular connector 32, does not exceed 4 0 mm. The design of the tubular connector 32 provides patients with the option to decide whether to connect the hose 3, thus affording them greater freedom of choice.

The foregoing represents merely a preferred embodiment of this disclosure and should not be construed as limiting the scope of the disclosure. Any modifications, equivalent substitutions, and improvements made within the spirit and principles of the present disclosure shall be deemed to fall within the protective scope of this disclosure.

The benefits of the modular elbow frame assembly 1 for a ventilator provided by this disclosure can include:

1) By employing a detachable, modular design for the elbow 2, the assembly accommodates the diverse requirements and preferences of patients with OSA concerning air pressure. This design elevates the comfort of treatment, enabling patients to choose between elbows 2 of varying diameters or numbers of exhaust holes to adjust airflow pressure, particularly when the ventilator fails to deliver the ideal pressure conditions. Given that patients have distinct airflow pressure requirements, this disclosure allows patients to select an elbow that aligns with their needs, making CPAP therapy more comfortable. Furthermore, this disclosure provides specialized options for patients experiencing respiratory insufficiency or failure, offering the choice to opt for a hole-free elbow 2 to better accommodate their unique circumstances.

2) The quick-release feature of this design improves the flexibility and convenience for patients undergoing therapy, facilitating the swift detachment of the elbow 2 from the frame 8 or patient interface cushions 7, including a nasal mask, a full-face mask, a nasal pillow, or a nasal cradle mask. By adding releasable functions among the therapeutic components, the design simplifies the routine of donning and doffing, particularly beneficial for patients who need to rise at night or momentarily step away from their resting area. And it eliminates the need for cumbersome steps such as unfastening head straps 5 or extracting the patient interface cushion 7, thereby streamlining laborious adjustment procedures. Moreover, the design ensures a releasable yet stable connection between the elbow 2 and the frame 8 or patient interface cushions 7, supplemented by the capability for mutual rotation. The second connector 24 of the elbow 2, configured to rotate in relation to the hose 3 or the tubular connector 32, thereby improving patient maneuverability. Such features accommodate diverse wearing preferences, prevent the inconvenience of hose 3 tangling, and overall, heighten the user experience by providing increased comfort and ease of use for patients.

3) The modular design of an external connecting component 21 that allows for the detachable connection with the elbow 2 empowers patients with the flexibility to incorporate or forgo the noise reduction element 41, catering to individual preferences. For those disinclined towards noise reduction materials, the structure allows for straightforward disassembly. If the external connecting component 21 or noise reduction materials incur damage, they can be replaced separately without the need to substitute the entire elbow 2 unit. This not only enhances the durability of the elbow 2 but also simplifies its maintenance. Furthermore, patients can select from an assortment of noise reduction materials, such as noise reduction cotton or noise reduction mesh, allowing them to opt for different noise reduction effects and usage experiences. The user-friendly, detachable design also addresses common hygiene concerns, eliminating hard-to-clean recesses and ensuring that all components are replaceable, promoting a cleaner, more sanitary usage environment.

4) The modular elbow 2 design provides patients with different connection alternatives, featuring a detachable connection between the second connector 24 of the elbow 2 and the hose 3. This allows patients to choose between attaching the hose 3 to the elbow 2 prior to connecting the hose 3 to the ventilator tube, or utilizing a tubular connector 32 appropriate for the specific diameter of the ventilator tube port to establish a direct link between the elbow 2 and the ventilator tube. Factors like the hose 3 length and tube size can influence user experience of patients. Some might appreciate an extended hose 3 for greater mobility, while others might prefer the enhanced airflow from the ventilator tube. The use of a tubular connector 32 grants patients greater autonomy to select the configuration that maximizes their comfort during therapy, offering different options for patients with various preferences, enhancing user-friendliness and providing more choices for the patients. Furthermore, this design also reduces the need for complete component replacements, decreasing carbon dioxide emissions. Additionally, the modular detachable design is space-efficient during logistics and transportation by allowing uniform stacking and it also aligns with sustainable and eco-friendly design principles.

It must be noted that as used herein and in the appended claims, the singular forms "a", "an", and "the" include their plural equivalents, unless the context clearly dictates otherwise.

The invention claimed is:

1. A modular elbow frame assembly for a ventilator, configured to provide positive pressure breathing gas to an airway of a patient, the modular elbow frame assembly comprising:
   a hose for connection to a ventilator tube,
   an elbow that connects the hose and a frame or a patient interface cushion for a delivery of pressurized gas to the airway, and
   a quick-release device to detachably connect the elbow and the patient interface cushion;

wherein the elbow includes a first connector and a second connector, a junction between the first connector and the second connector being curved;

wherein the quick-release device is provided on the first connector of the elbow and protruding pieces of the quick-release device are integrally formed with the first connector of the elbow, and the first connector is detachably connected with the frame or the patient interface cushion by the quick-release device;

wherein one end of the hose is detachably connectable to the second connector of the elbow, an other end is connectable to the ventilator tube, and the hose is configured to channel the pressurized gas through the elbow into the airway for respiration;

wherein at least one vent is provided on the elbow, and the at least one vent is configured to release a continuous flow of exhaled gas from the patient to an external environment, wherein the at least one vent on the elbow includes several exhaust holes to facilitate communication between the elbow and the external environment and to allow for the exhaled gas from the patient to be emitted outside the elbow, with:

a maximum total area of the exhaust holes not exceeding 5 cm$^2$;

a weight of no more than 20 g for the elbow;

a portion of an outer wall of the second connector fitting against an inner wall of the hose upon a connection of the elbow with the hose, wherein the frame includes a fixed opening for connection with the elbow, the fixed opening includes a receiving structure configured to receive the quick-release device on the elbow, and wherein the fixed opening has an area of the fixed opening at or between 5% to 50% of an external surface area of the frame not facing a face of the patient.

2. The modular elbow frame assembly for a ventilator according to claim 1, wherein the quick-release device includes a pair of the protruding pieces, each respectively provided on two sides of the first connector and extending outward, with two front ends forming hook sections, and the patient interface cushion includes a fixed part for attachment and coverage by the hook sections, with an annular positioning arm on an outer edge surface of the first connector, and the fixed part of the patient interface cushion embeds into the annular positioning arm and the hook sections to facilitate a rotational connection between the patient interface cushion and the first connector.

3. The modular elbow frame assembly for a ventilator according to claim 1, wherein the hose includes a first end nearer the elbow, a second end away from the elbow, and a spiral tube provided between the first end and the second end, the spiral tube including several adjacent coils, the hose detachably connecting to the elbow through the first end and channeling gas pressurized by the ventilator into the patient's airway.

4. The modular elbow frame assembly for a ventilator according to claim 3, wherein the elbow and the first end of the hose are detachably connected through a snap-fit.

5. The modular elbow frame assembly for a ventilator according to claim 3, wherein the elbow and the first end of the hose are detachably connected through magnetic attraction.

6. The modular elbow frame assembly for a ventilator according to claim 3, wherein the second end of the hose connects to the ventilator tube, and a rotating component is provided on the second end of the hose to provide a rotational connection between the hose and the ventilator tube.

7. The modular elbow frame assembly for a ventilator according to claim 1, wherein an axis of the exhaust holes forms an angle $\alpha$ of at or between 0 to 45° with a vertical symmetrical axis of the first connector of the elbow to guide the exhaled gas from the patient to the external environment.

8. A modular elbow frame assembly for a ventilator, configured to provide positive pressure breathing gas an airway of a patient, the modular elbow frame assembly comprising:

a tubular connector for connection to a ventilator tube, an elbow that connects the tubular connector and a patient interface cushion for a delivery of pressurized gas to the airway, and a quick-release device to detachably connect the elbow and the patient interface cushion;

wherein the elbow includes a first connector and a second connector, and a junction between the first connector and the second connector is curved;

wherein the tubular connector is detachably connectable to the second connector of the elbow, the second connector and the tubular connector join to create an airflow passage to receive and transport the positive pressure breathing gas from the ventilator tube to the patient through the patient interface cushion;

wherein at least one vent is provided on the elbow, and the at least one vent is configured to release a continuous flow of exhaled gas from the patient to an external environment, wherein the at least one vent on the elbow includes several exhaust holes to facilitate communication between the elbow and the external environment and to allow for the exhaled gas from the patient to be emitted outside the elbow, wherein a ratio, whether calculated as a diameter of an outer interface that contacts external air divided by a diameter of an inner interface devoid of such contact, or vice versa, is less than 2.45 for at least part of the exhaust holes;

wherein an axis of the exhaust holes forms an angle between 0 to 45° with a symmetrical axis of the first connector of the elbow and wherein the fixed opening has an area of the fixed opening at or between 5% to 50% of an external surface area of the frame not facing a face of the patient.

9. The modular elbow frame assembly for a ventilator according to claim 8, wherein the tubular connector includes a first port connectable to the ventilator tube and a second port connectable to the elbow, the tubular connector being detachably connectable to the ventilator tube and the elbow through the first port and the second port.

10. The modular elbow frame assembly for a ventilator according to claim 9, wherein an inner diameter or an outer diameter of the first port of the tubular connector corresponds to an outer diameter or an inner diameter of the second connector for connecting the same so that the positive pressure breathable gas passes through the tubular connector in a sealed manner.

11. The modular elbow frame assembly for a ventilator according to claim 9, wherein the first port connectable to the ventilator tube has a diameter of 22 mm or 15 mm, compatible with the ventilator tube.

12. A modular elbow frame assembly for a ventilator, configured to provide positive pressure breathing gas to an airway of a patient, the modular elbow frame assembly comprising:

a hose for connection to a ventilator tube, an elbow that connects the hose and a frame or a patient interface cushion for a delivery of pressurized gas to the airway of the patient, and a quick-release device to detachably connect the elbow and the patient interface cushion;

wherein the elbow includes a first connector and a second connector, wherein a junction between the first connector and the second connector is curved, and wherein an outer diameter of the first connector of the elbow is equal to or greater than 10 mm;

wherein the quick-release device is provided on the first connector of the elbow and protruding pieces of the quick-release device are integrally formed with the first connector of the elbow, wherein the first connector detachably connects to the frame or the patient interface cushion by the quick-release device, and wherein a length of the quick-release device is between 0.5 mm to 35 mm;

wherein one end of the hose is detachably connectable to the second connector of the elbow, an other end is connectable to the ventilator tube, and the hose is configured to channel the pressurized gas through the elbow into the airway of the patient for respiration;

wherein at least one vent is provided on the elbow, and the at least one vent is configured to release a continuous flow of exhaled gas from the patient to an external environment;

wherein the at least one vent on the elbow includes several exhaust holes to facilitate communication between the elbow and the external environment and to allow for the exhaled gas from the patient to be emitted outside the elbow, and wherein the fixed opening has an area of the fixed opening at or between 5% to 50% of an external surface area of the frame not facing a face of the patient.

13. The modular elbow frame assembly for a ventilator according to claim 12, wherein a central axis of the first connector and a central axis of the second connector form an angle between 10° to 170°.

14. The modular elbow frame assembly for a ventilator according to claim 12, wherein the modular elbow frame assembly further comprises an external connecting component provided with a noise reduction element.

15. The modular elbow frame assembly for a ventilator according to claim 14, wherein the noise reduction element includes a noise reduction cotton or a noise reduction mesh, wherein the noise reduction cotton includes one of fibrous sound-absorbing material or foam sound-absorbing material, and the noise reduction mesh includes one of fabric or nylon.

16. A modular elbow frame assembly for a ventilator, configured to provide positive pressure breathing gas to an airway of a patient, the modular elbow frame assembly comprising:

a tubular connector for connection to a ventilator tube, an elbow that connects the tubular connector and a patient interface cushion for a delivery of pressurized gas to the airway of the patient, and a quick-release device to detachably connect the elbow and the patient interface cushion;

wherein the elbow includes a first connector and a second connector, wherein a junction between the first connector and the second connector is curved, and wherein the first connector of the elbow is integrally formed with protruding pieces of the quick-release device;

wherein the tubular connector is detachably connectable to the second connector of the elbow, when the two are connected, the second connector and the tubular connector jointly create an airflow passage to receive and transport the positive pressure breathing gas from the ventilator tube to the patient through the patient interface cushion;

wherein at least one vent is provided on the elbow, and the at least one vent is configured to release a continuous flow of exhaled gas from the patient to an external environment; and wherein the at least one vent on the elbow includes several exhaust holes to facilitate communication between the elbow and the external environment and to allow for the exhaled gas from the patient to be emitted outside the elbow;

and wherein the fixed opening has an area of the fixed opening at or between 5% to 50% of an external surface area of the frame not facing a face of the patient.

17. The modular elbow frame assembly for a ventilator according to claim 16, wherein an outer diameter of the tubular connector is 15 mm or 22 mm.

18. The modular elbow frame assembly for a ventilator according to claim 16, wherein the tubular connector includes one or more of the following materials: polycarbonate, polyethylene, polypropylene, silicone and thermoplastic elastomer.

19. The modular elbow frame assembly for a ventilator according to claim 16, wherein front ends of the protruding pieces form hook sections to connect to the patient interface cushion.

* * * * *